US008876686B2

(12) United States Patent
Heilman et al.

(10) Patent No.: US 8,876,686 B2
(45) Date of Patent: Nov. 4, 2014

(54) CONTROL OF BLOOD FLOW ASSIST SYSTEMS

(75) Inventors: Marlin Stephen Heilman, Sarver, PA (US); Douglas J. Koebler, Irwin, PA (US); Charles Robert Kohler, Cheswick, PA (US); Jon David Wagner, Pittsburgh, PA (US); David M. Reilly, Pittsburgh, PA (US)

(73) Assignee: Vascor, Inc, Pittsburgh, PA (US)

( * ) Notice: Subject to any disclaimer, the term of this patent is extended or adjusted under 35 U.S.C. 154(b) by 0 days.

(21) Appl. No.: 13/370,155

(22) Filed: Feb. 9, 2012

(65) Prior Publication Data

US 2013/0041204 A1 Feb. 14, 2013

Related U.S. Application Data

(60) Provisional application No. 61/444,532, filed on Feb. 18, 2011, provisional application No. 61/444,414, filed on Feb. 18, 2011, provisional application No. 61/444,510, filed on Feb. 18, 2011.

(51) Int. Cl.
*A61N 1/365* (2006.01)
*A61M 1/12* (2006.01)
*A61M 1/10* (2006.01)
*A61M 39/22* (2006.01)

(52) U.S. Cl.
CPC ............... *A61M 1/10* (2013.01); *A61M 1/122* (2014.01); *A61M 1/1087* (2014.01); *A61M 2039/226* (2013.01); *A61M 2039/224* (2013.01); *A61M 39/22* (2013.01); *A61M 39/223* (2013.01); *A61M 1/1086* (2013.01)
USPC ......................................................... 600/17

(58) Field of Classification Search
CPC .............. A61M 1/1087; A61M 2039/226; A61M 2039/224; A61M 39/223; A61M 1/1086; A61M 1/10; A61M 39/22; A61M 1/122

USPC ........................................................... 600/17
See application file for complete search history.

(56) References Cited

U.S. PATENT DOCUMENTS 1,222,534 A 4/1917 Cormier
3,136,257 A 6/1964 Smith (Continued)

FOREIGN PATENT DOCUMENTS

DE 3901470 8/1980
EP 1129736 A1 9/2001

(Continued)

OTHER PUBLICATIONS

Nitta, S. et al., "The Newly Designed Univalved Artificial Heart," ASAIO Transactions Vo. 37, No. 3, M240-M241 (1991).

*Primary Examiner* — Carl H Layno
*Assistant Examiner* — Erin Piateski
(74) *Attorney, Agent, or Firm* — Bartony & Associates, LLC.

(57) ABSTRACT

In one aspect, an implantable pump system for assisting blood flow in a patient includes a blood flow path comprising a flexible conduit, at least one valve in fluid connection with the flexible conduit, a drive system in operative connection with the valve to move the valve in a reciprocating manner, an implantable control system and at least one sensor in communicative connection with the control system. The sensor is adapted to measure at least one property of blood. The control system is adapted to control movement of the valve on the basis of data regarding position of the valve with respect to time or a derivative thereof (that is, position, velocity, acceleration or a derivative thereof) in combination with data of the measured at least one property of blood from the sensor.

6 Claims, 20 Drawing Sheets

(56) References Cited

U.S. PATENT DOCUMENTS

| | | | |
|---|---|---|---|
| 3,513,845 A * | 5/1970 | Callaghan et al. | 604/6.1 |
| 3,553,736 A | 1/1971 | Kantrowitz | |
| 3,692,018 A | 9/1972 | Goetz | |
| 3,717,153 A * | 2/1973 | Bowers | 607/27 |
| 3,842,440 A | 10/1974 | Karlson | |
| 3,911,897 A | 10/1975 | Leachman, Jr. | |
| 3,919,722 A * | 11/1975 | Harmison | 623/3.16 |
| 4,034,742 A | 7/1977 | Thoma | |
| 4,051,840 A | 10/1977 | Kantrowitz | |
| 4,195,623 A | 4/1980 | Zeff | |
| 4,210,409 A | 7/1980 | Child | |
| 4,245,622 A | 1/1981 | Hutchins, IV | |
| 4,334,180 A | 6/1982 | Bramm | |
| 4,543,954 A * | 10/1985 | Cook et al. | 607/21 |
| 4,618,789 A | 10/1986 | Flisikowski | |
| 4,726,383 A * | 2/1988 | Cook et al. | 607/21 |
| 4,733,652 A | 3/1988 | Kantrowitz | |
| 4,813,952 A * | 3/1989 | Khalafalla | 623/3.12 |
| 4,901,725 A * | 2/1990 | Nappholz et al. | 607/17 |
| 4,925,377 A | 5/1990 | Inacio | |
| 5,024,222 A * | 6/1991 | Thacker | 607/22 |
| 5,108,426 A | 4/1992 | Biro | |
| 5,147,281 A | 9/1992 | Thornton | |
| 5,266,012 A | 11/1993 | Hashimoto | |
| 5,348,123 A | 9/1994 | Takahashi | |
| 5,545,216 A | 8/1996 | Bokros | |
| 5,676,162 A | 10/1997 | Larson, Jr. | |
| 5,676,651 A | 10/1997 | Larson, Jr. | |
| 5,722,930 A | 3/1998 | Larson, Jr. | |
| 5,758,666 A * | 6/1998 | Larson et al. | 128/899 |
| 5,800,472 A * | 9/1998 | Mann | 607/29 |
| 6,112,119 A * | 8/2000 | Schuelke et al. | 607/9 |
| 6,375,607 B1 | 4/2002 | Prem | |
| 6,511,412 B1 * | 1/2003 | Freed et al. | 600/17 |
| 7,588,530 B2 | 9/2009 | Heilman | |
| 7,614,998 B2 * | 11/2009 | Gross et al. | 600/17 |
| 7,662,084 B2 | 2/2010 | Sun | |
| 2003/0229380 A1 * | 12/2003 | Adams et al. | 607/9 |
| 2003/0233143 A1 | 12/2003 | Gharib | |
| 2004/0044374 A1 * | 3/2004 | Weinberg et al. | 607/25 |
| 2004/0097782 A1 | 5/2004 | Korakianitis | |
| 2005/0131271 A1 * | 6/2005 | Benkowski et al. | 600/16 |
| 2005/0131474 A1 * | 6/2005 | Jenkins et al. | 607/11 |
| 2006/0247704 A1 * | 11/2006 | Sun et al. | 607/17 |
| 2006/0252977 A1 * | 11/2006 | Sullivan | 600/16 |
| 2007/0185369 A1 * | 8/2007 | Mirhoseini et al. | 600/16 |
| 2007/0288063 A1 * | 12/2007 | de Voir et al. | 607/28 |
| 2010/0191036 A1 * | 7/2010 | Sullivan | 600/16 |

FOREIGN PATENT DOCUMENTS

| | | |
|---|---|---|
| EP | 1338294 A2 | 8/2003 |
| WO | WO2006020273 A2 | 2/2006 |
| WO | WO2012112378 A2 | 8/2012 |

* cited by examiner

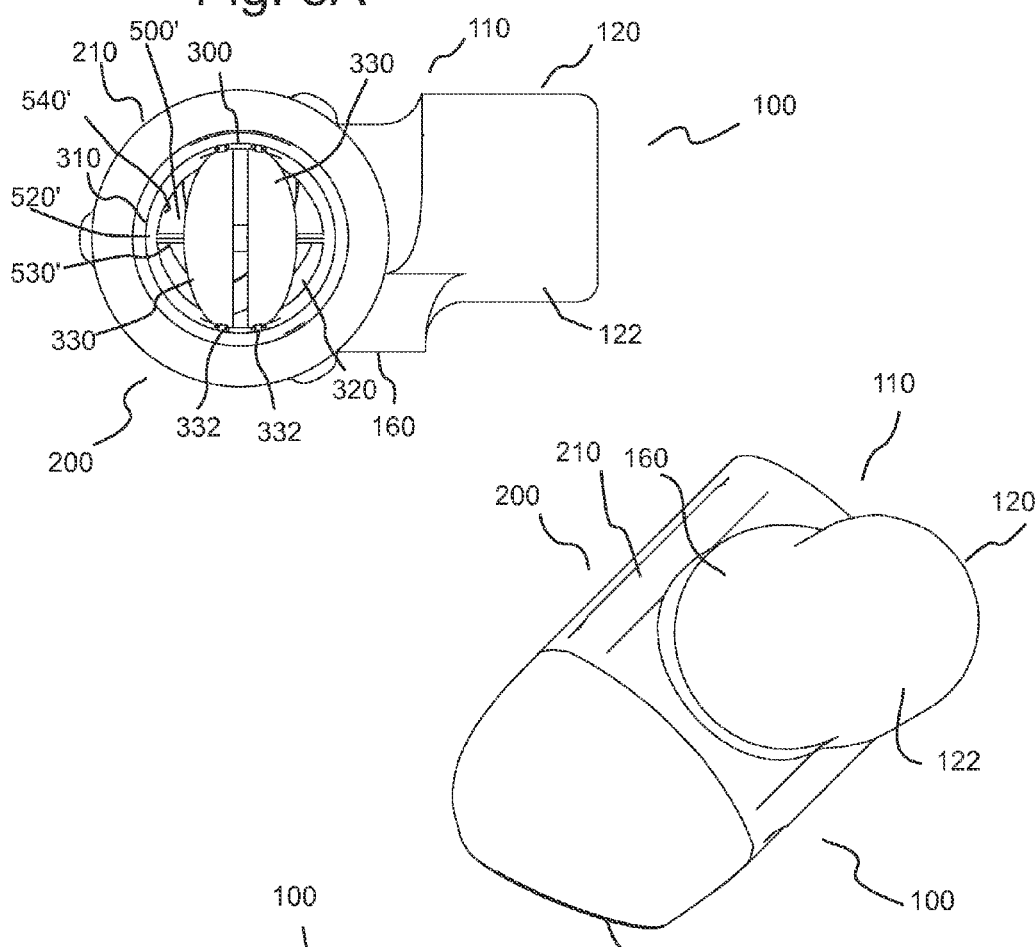
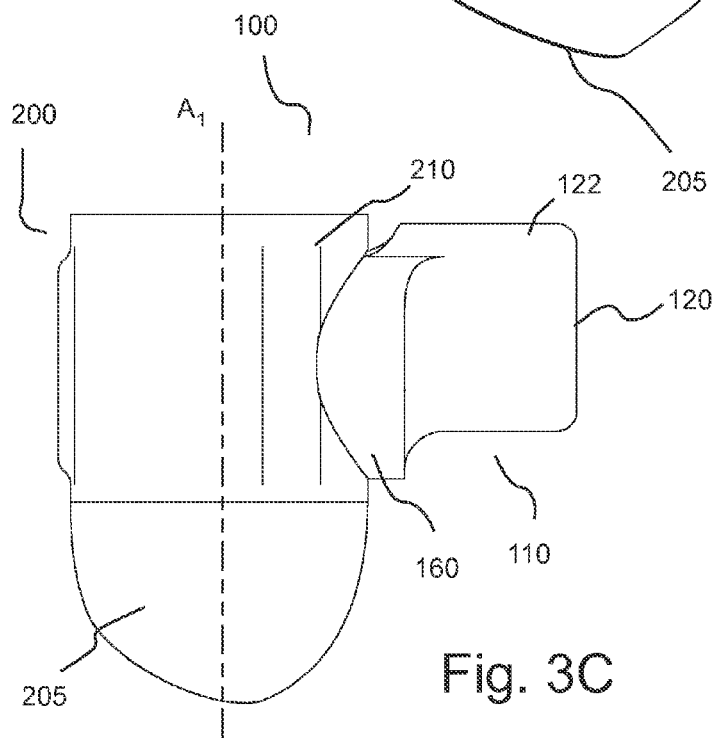

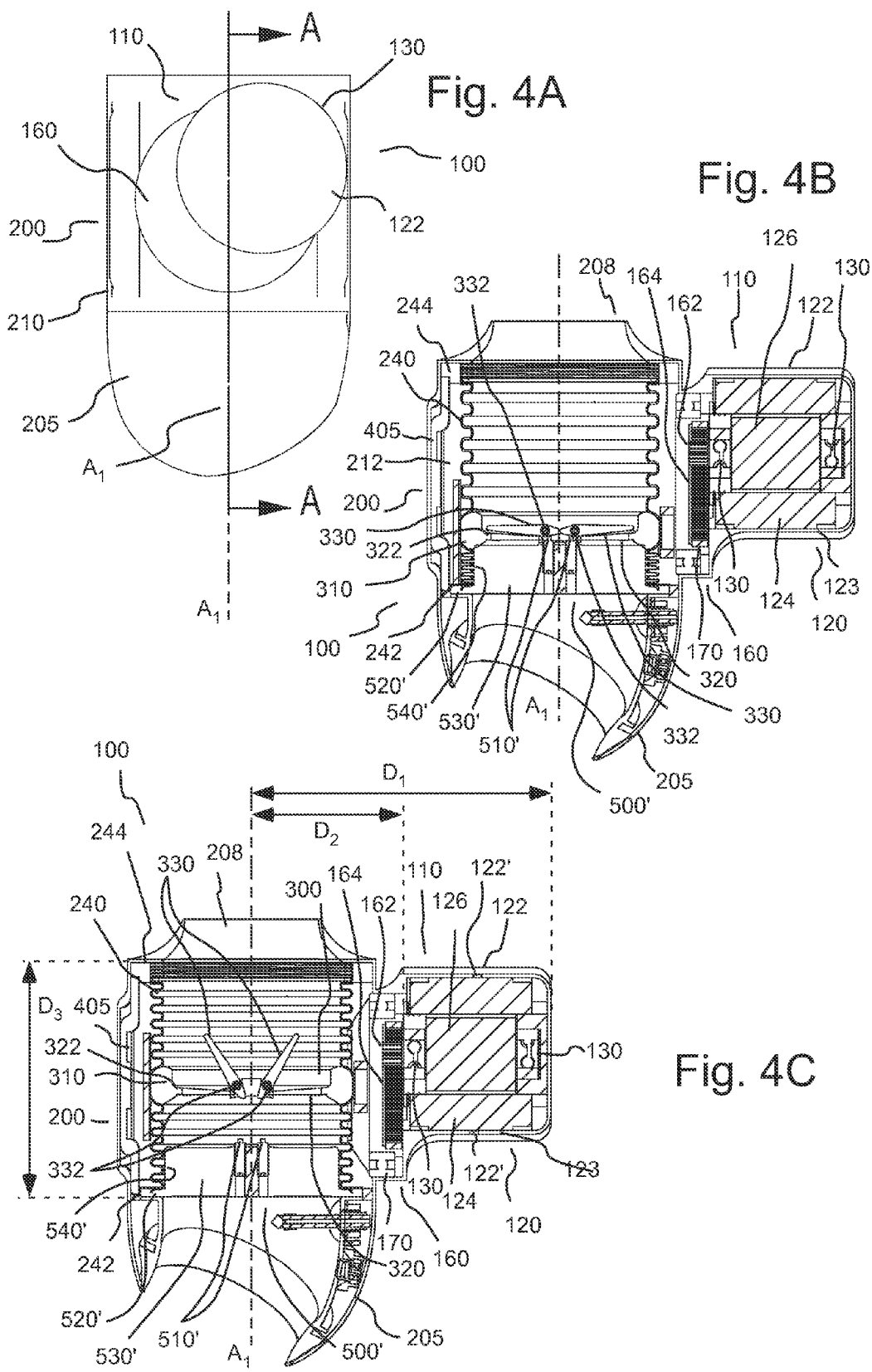

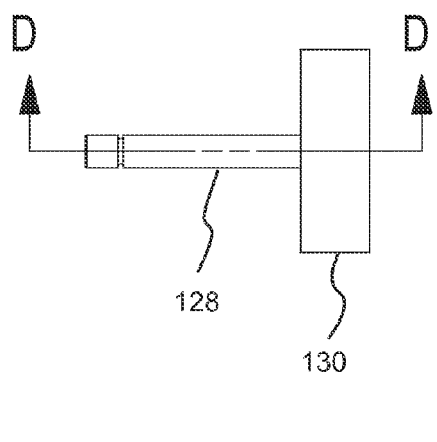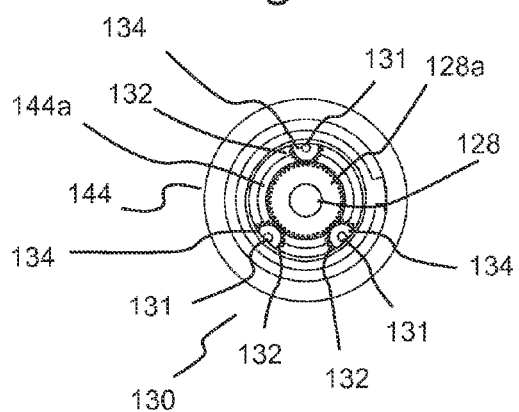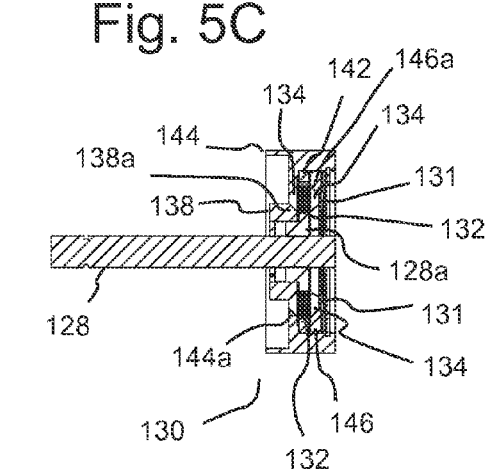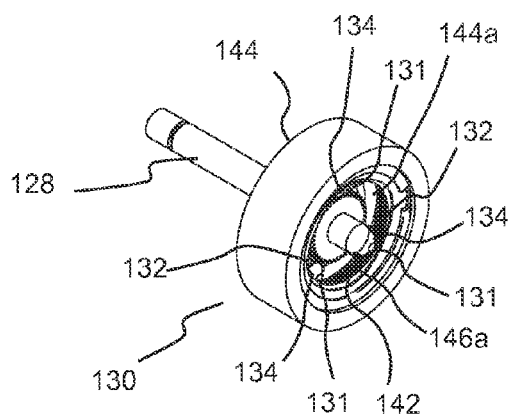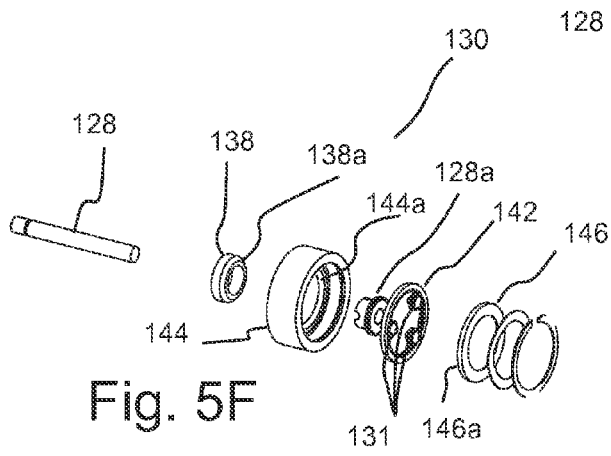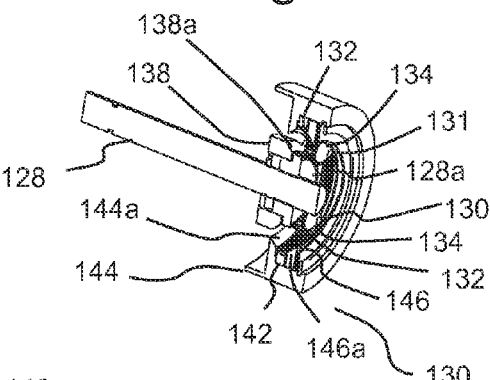

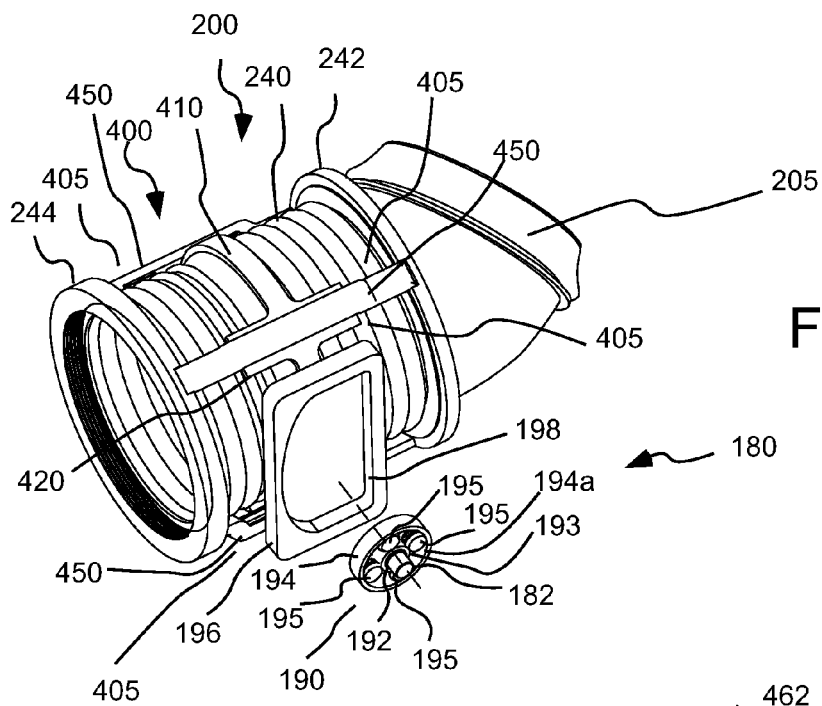
Fig. 6C
Fig. 6E
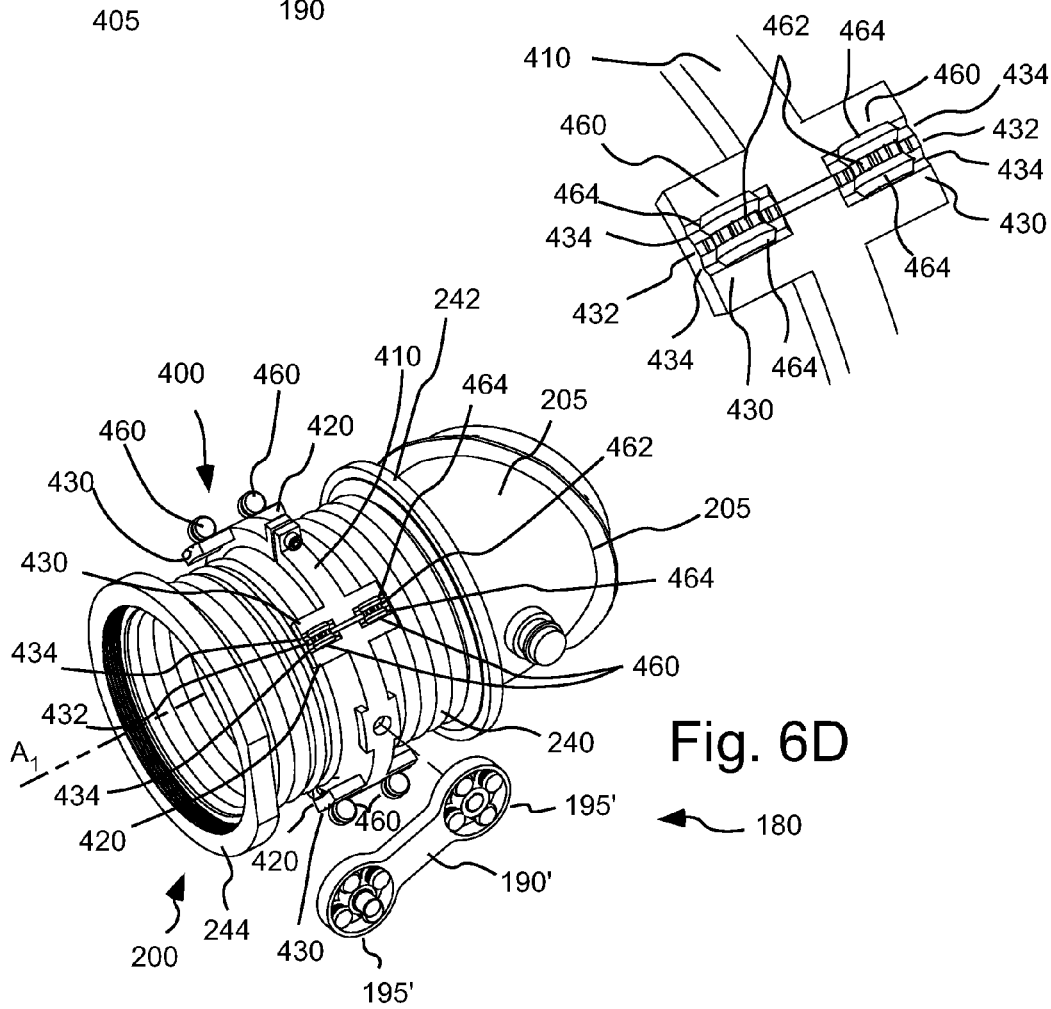
Fig. 6D

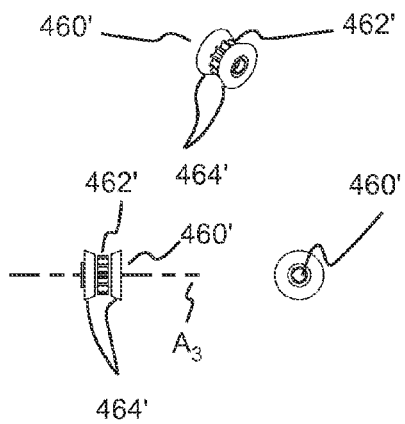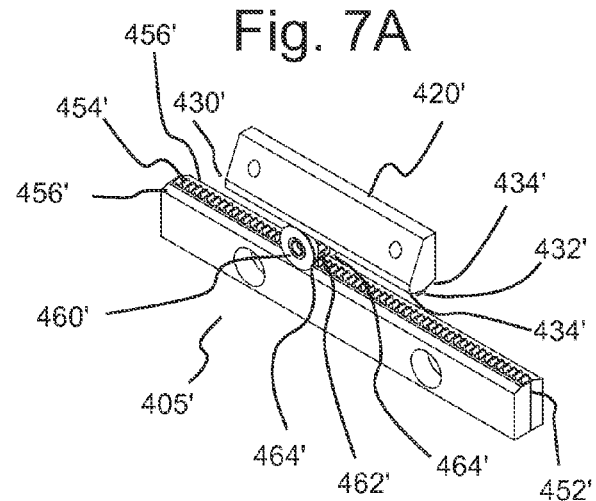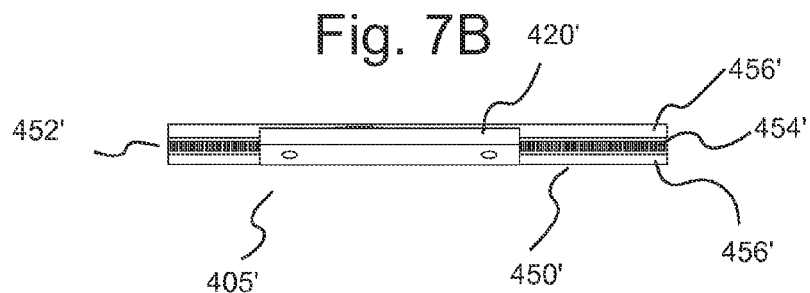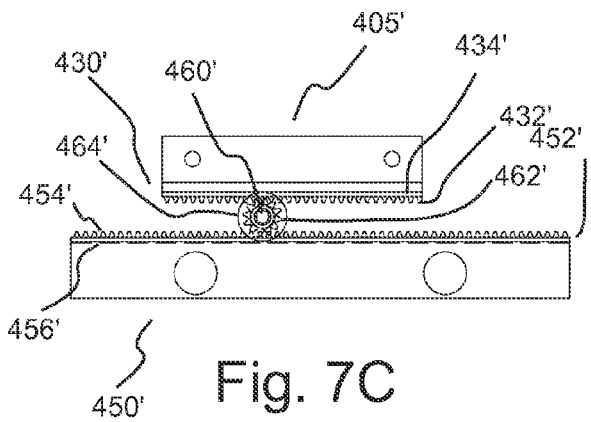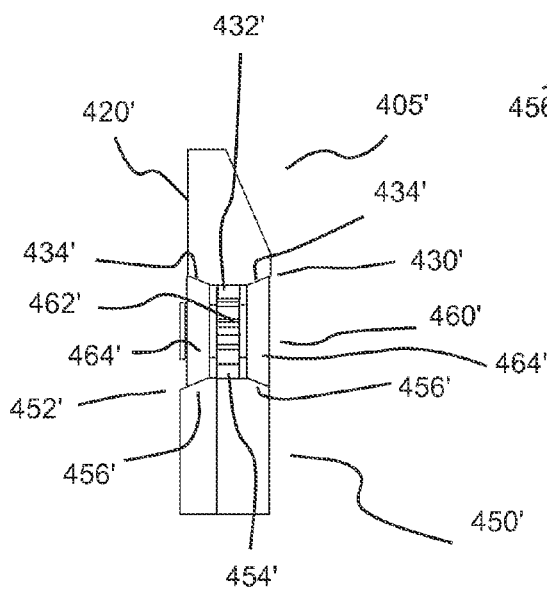

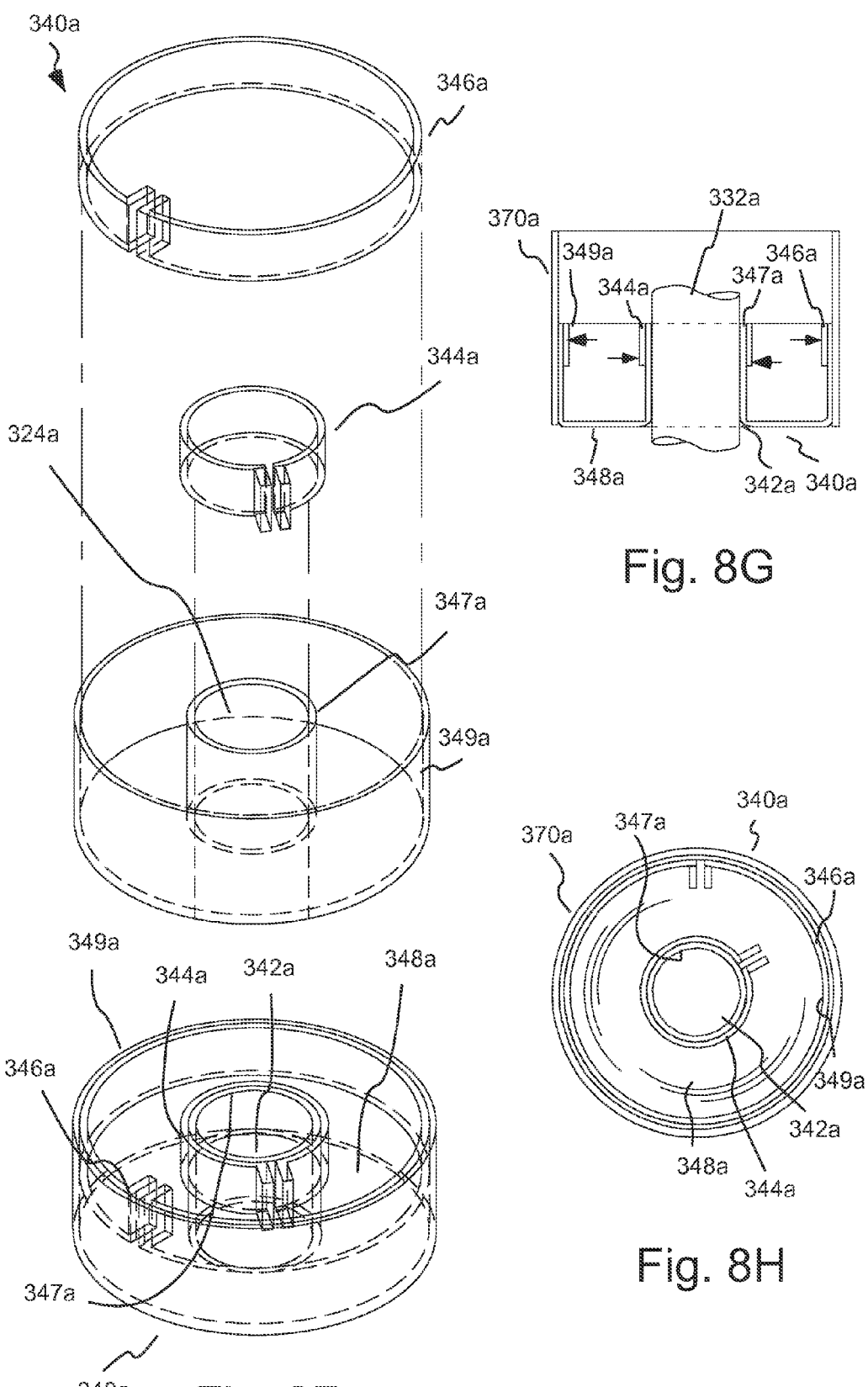

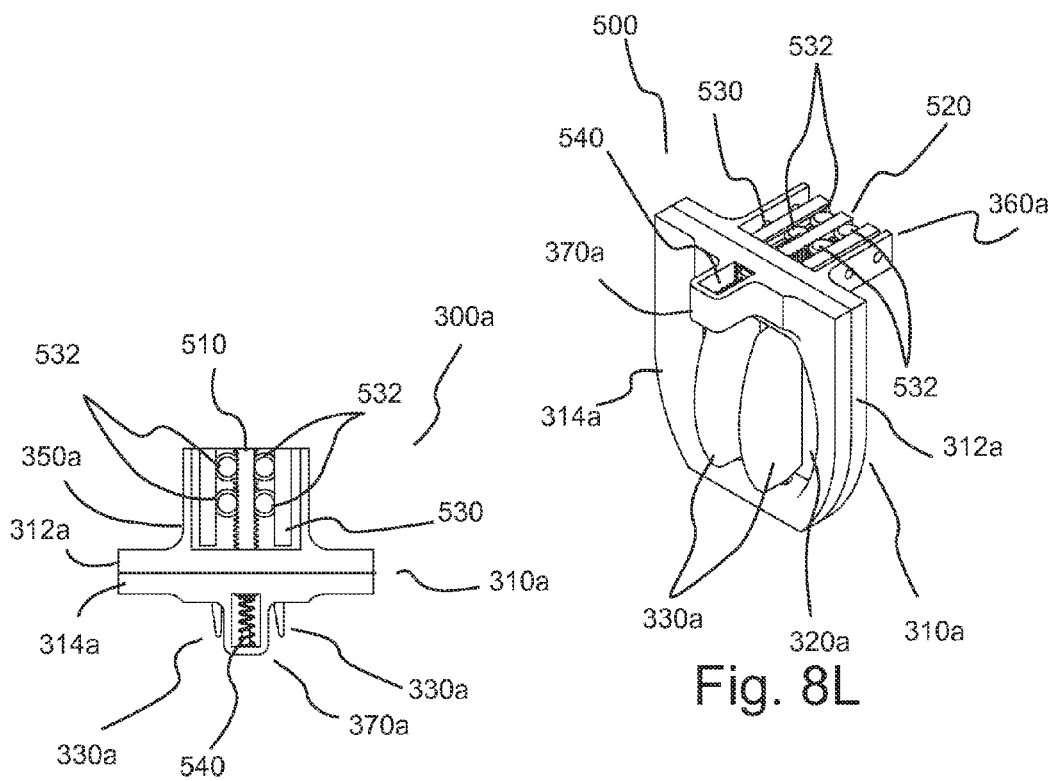
Fig. 8L
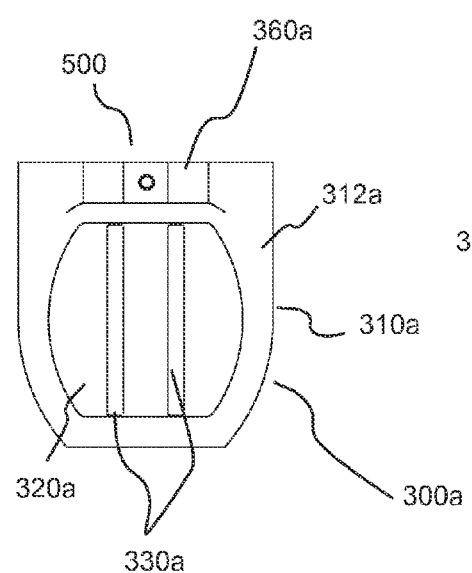
Fig. 8K
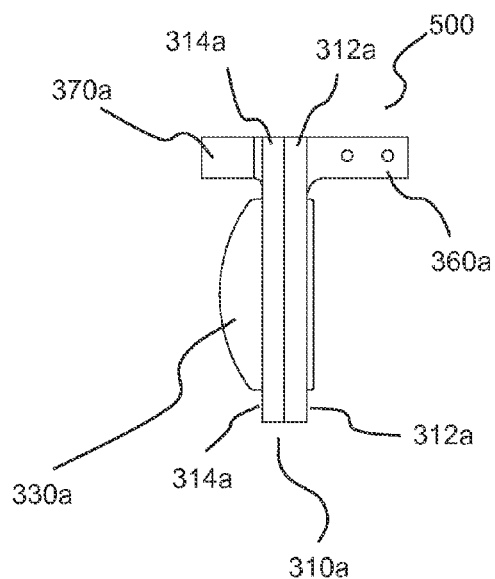
Fig. 8N
Fig. 8M

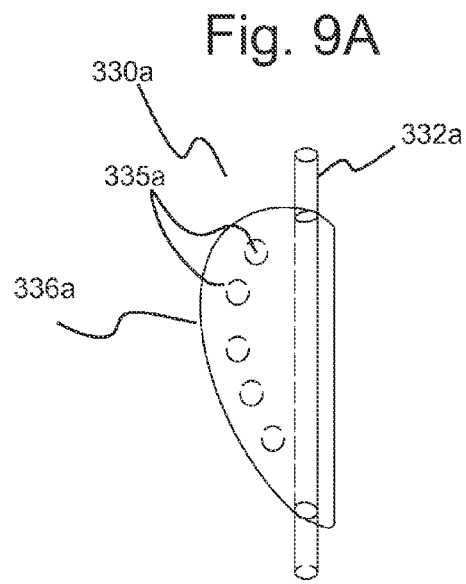
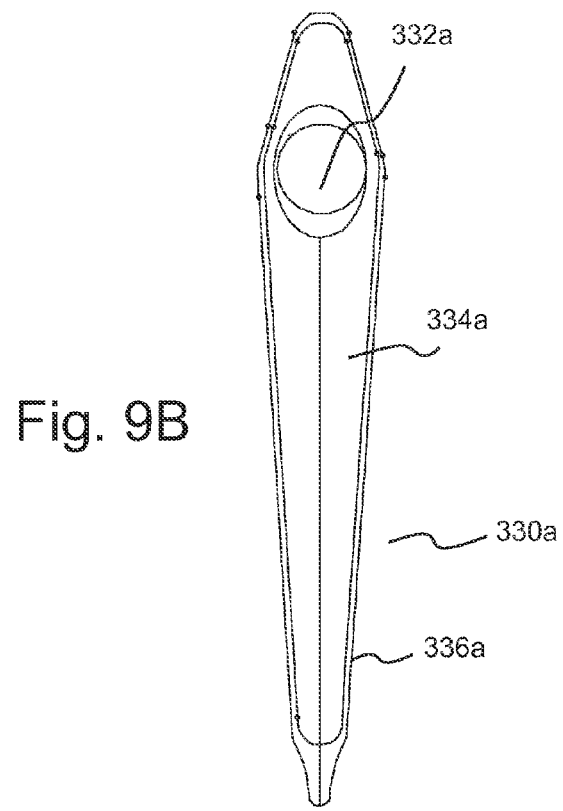
Fig. 9A
Fig. 9B
Fig. 9C    Fig. 9D    Fig. 9E
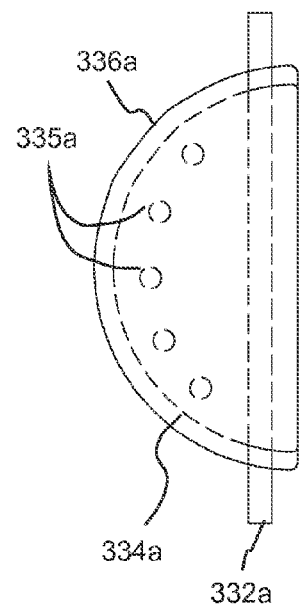
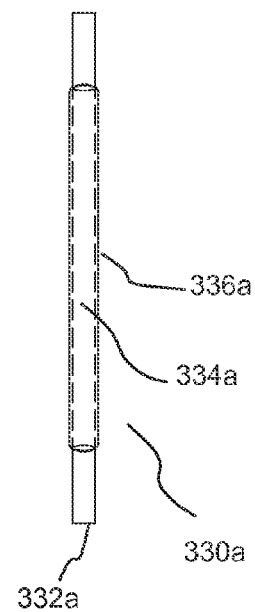
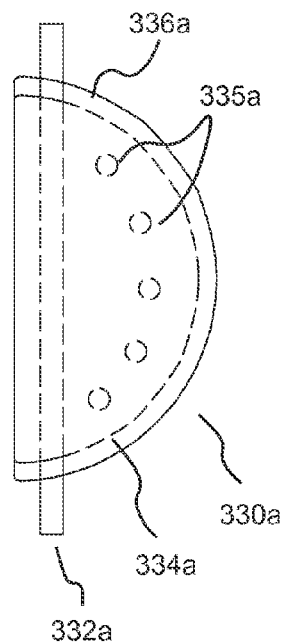

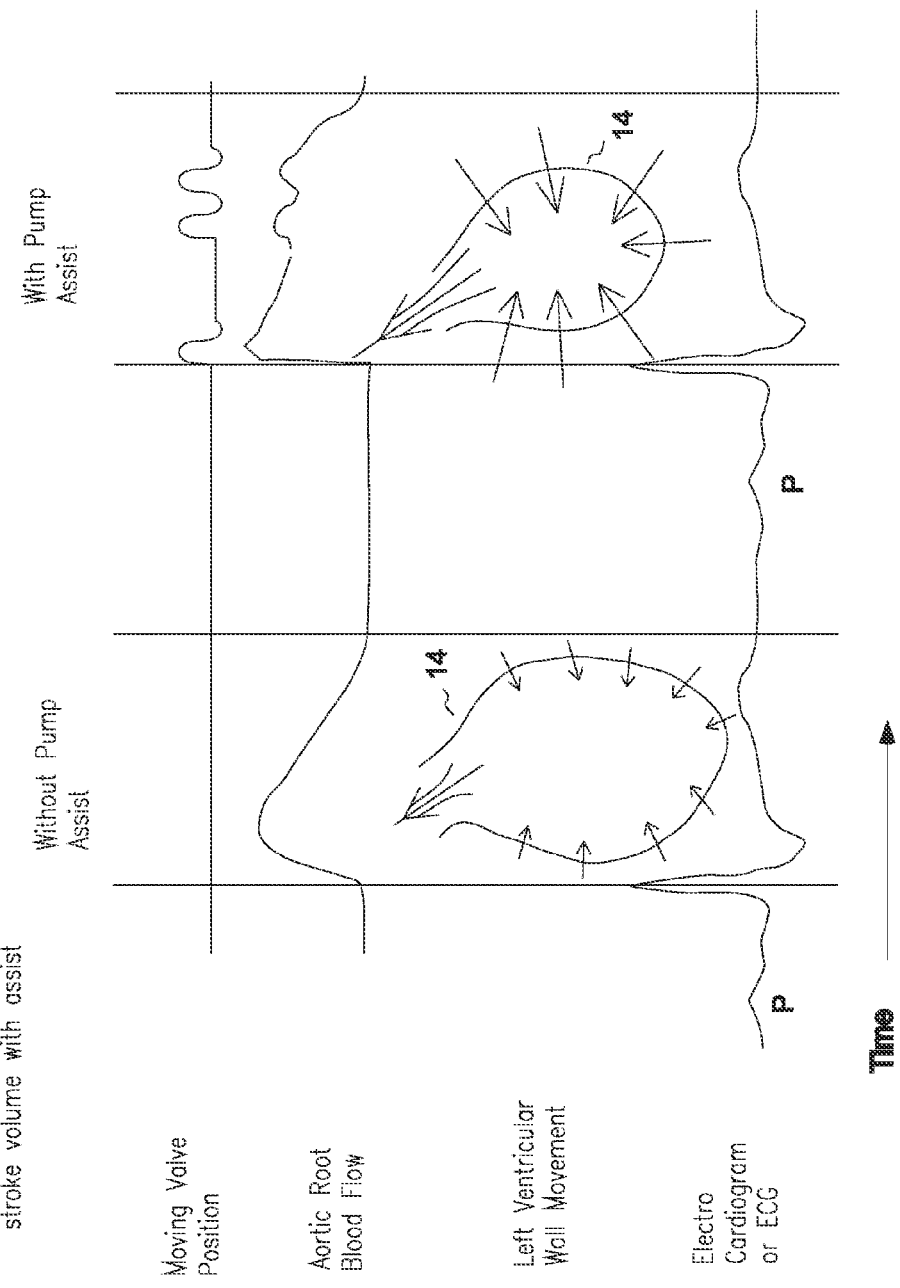

CONTROL OF BLOOD FLOW ASSIST SYSTEMS

CROSS REFERENCE TO RELATED APPLICATION

This application claims benefit of U.S. Patent Application Ser. No. 61/444,414, filed Feb. 18, 2011, U.S. Patent Application Ser. No. 61/444,510, filed Feb. 18, 2011, and U.S. Provisional Patent Application Ser. No. 61/444,532, filed Feb. 18, 2011, the disclosures of which are incorporated herein by reference.

BACKGROUND

The following information is provided to assist the reader to understand the technology described below and certain environments in which such technology can be used. The terms used herein are not intended to be limited to any particular narrow interpretation unless clearly stated otherwise in this document. References set forth herein may facilitate understanding of the technology or the background thereof. The disclosure of all references cited herein are incorporated by reference.

Heart failure, or the inability of the heart to pump sufficient blood for the body's needs, results in very poor quality of life, huge costs to society, and hundreds of thousands of yearly deaths. Heart failure is caused by an abnormally low cardiac output. Cardiac output is the outflow of blood from the heart and can be measured in liters of blood flow per minute or LPM. Cardiac output for a normal man at rest or during light activity is approximately 5 liters per minute. Severe heart failure exists when the cardiac output is between approximately 2.5 to 3.5 liters per minute. For an average man in heart failure having a heart rate of 80 beats per minute, the average amount of blood that is pumped with each heartbeat (sometimes referred to as stroke volume) might, for example, be 37 milliliters or ml. If the same man was not in heart failure, his heart might, for example, pump 62 milliliters with each heartbeat. An effective treatment for such heart failure would be to increase the low, 37 ml stroke volume up to the normal, 62 ml stroke volume.

The main pumping chamber of the heart or left ventricle or LV, which has an inlet mitral valve and an outlet aortic valve. During left ventricular contraction or systole, the inlet valve closes as blood is pushed through the aortic valve into the aorta or main artery to the body. When the LV is resting during diastole, LV pressure may be between 2 and 20 mm of Hg pressure. This diastolic pressure is termed the LV preload. The preload will be in the higher end of its pressure range during heart failure. During active LV contraction or systole, the LV must eject its blood against the pressure in the aorta. Aortic pressure is typically between 70 and 140 mm Hg Pressure. This aortic pressure is termed the after-load. It is well known that, if the after-load is reduced in heart failure, the LV stroke volume will naturally increase and this increase is one reason that afterload-reducing drugs such as ACE-inhibitors help heart failure patients.

Heart failure is generally caused by one of two disease mechanisms. The first is a physical weakness of LV muscular contraction, typically as a result of LV muscle damage from one or more heart attacks. Heart failure resulting from a weak heart muscle combined with more than adequate blood volume stored in the LV at the beginning of the systolic muscular contraction for producing a normal stroke volume is termed "systolic failure". In systolic failure, the ratio or fraction of the ejected stroke volume compared to the starting LV blood volume is low. This fraction is known as the ejection fraction or EF. Normal EFs are in the range of 55 to 65 percent, but with systolic heart failure, EFs are typically in the 10 to 40 percent range.

A second form of heart failure is known as "heart failure having preserved ejection fraction", or by the somewhat outdated term, "diastolic failure". In diastolic failure, the heart muscle is abnormally stiff and the heart is not able to adequately fill with blood. The stroke volumes in heart failure having preserved ejection fraction are lower than normal, but the EF is normal or near normal.

Blood pumps which lower the aortic pressure after-load can be desirable because such pumps allow the failing LV to eject more blood with less effort. However, no commercially available afterload reducing devices have thus far been shown to be practical for extended support of the failing LV. Instead, all long term (that is, months to years), commercially available heart assist devices, whether rotary turbine pumps or collapsing chamber pumps, go around or bypass the failing LV, pumping blood from the LV apex through the pump into the aorta. By doing so, those pumps act in parallel to the LV and compete with the LV in their pumping action. This pumping competition has several negative complications including right heart failure, fusion of the aortic valve over time and the risk of collapsing the LV. Collapsing chamber pumps are physically large and thus cannot be implanted in some small patients. Rotary turbine pumps are desirably smaller, but have other limiting complications. For example, rotary turbine pumps induce high levels of shear stress in the blood elements and also may reduce the normal pulsatility of the blood entering the aorta. High shear stress on the blood cells promotes blood clotting which can lead to strokes and heart attacks. Physicians try to reduce this blood clotting by giving the patients anticoagulants, which, in turn, puts the patients at risk of excessive bleeding. These clotting and bleeding complications are substantial limitations to broader use of rotary turbine assist pumps.

A number of moving valve pumps have been disclosed for assisting blood flow. For example, U.S. Pat. Nos. 5,676,162, 5,676,651, and 5,722,930, disclose a single-stroke, moving valve pumps designed for ascending aortic placement. That device uses a commercially available artificial heart valve with attached magnets and requires excision of a portion of the aorta. A series of separate electric coils step the valve/magnet combination forward in a sliding action within a cylinder. The device is quite large for the limited space available between the heart and the take-off vessels from the aorta to the upper body and brain. The device is designed to have one stroke in synchronization with each LV systole. The blood volume required for closing commercially available heart valves is typically 2-5 ml and therefore multiple smaller oscillations per heart contraction in such devices would suffer from volumetric inefficiency. Another problem with such devices is the tight crevice between the cylinder wall and the moving valve. This tight space results in high blood shear and the corresponding risk of stroke or blood clotting complications if anti-coagulant therapy is necessary. The same problem exists with a moving valve pump disclosed in U.S. Pat. No. 4,210,409, which included two valves (one stationary and one moving).

U.S. Pat. No. 5,147,281 discloses an oscillatory valve blood pump that is external to the body and fits in an enclosure the size of a briefcase. The pump uses a stationary coil to attract a magnetic tube encasing a one-way valve. A forward stroke of the one-way valve propels blood until the tube assembly stops and is repelled backward by return leaf springs that are charged during the forward stroke. A second stationary valve is sometimes in the circuit. A stretchable silicone rubber tube connects the tube or pipe-valve assembly with the pump inlet and outlet.

Nitta, S. et al., "The Newly Designed Univalved Artificial Heart," ASAIO Transactions Vo. 37, No. 3, M240-M241 (1991) describes a "univalved artificial heart" powered electro-magnetically wherein the valve oscillates within a frequency range of 1 to 30 Hz. The valve is contained in a tube, with attached magnetic material. Stationary electric coils actuate the tube-magnet-valve combination. The valve is described as a jellyfish valve. A problem with jellyfish valves is the compound curvature or wrinkling of the membrane that occurs when the valve opens and closes. One can liken the action of the jellyfish valve to that of an umbrella that oscillates between a circular flat membrane and a wrinkled umbrella shape as it closes and opens. Wrinkling of the membrane is virtually impossible to prevent in a jellyfish valve and introduces stresses and strains that significantly limit the life of the valve.

U.S. Pat. No. 5,266,012 also uses a jellyfish valve in a vibrating pipe blood pump intended for use outside the body. Because the vibrating tube pump portion is separable from the drive mechanism. the blood-contacting portion of the pump is disposable.

U.S. Pat. No. 7,588,530, describes a moving valve pump having a curved blood flow path as well as a moving valve pump having a linear blood flow path. U.S. Pat. No. 7,588,530 discloses various drive mechanism to oscillate the moving valve in synchronization with the R wave of the patient's electrocardiogram. In the case of a pump having a linear blood flow path, a linear motor is disclosed to drive the moving valve thereof. U.S. Pat. No. 7,588,530 further discloses moving valves including a plurality of openings or ports wherein each port includes a resilient flap of material to open the port upon rearward movement of the moving valve and close the port upon forward movement of the moving valve. U.S. Pat. No. 7,588,530, further discloses movement of the moving valve thereof in the latter half of systole.

Numerous pharmacologic, biologic, and mechanical interventions have been devised to address heart disease/failure. Nonetheless, heart failure remains a major public health problem with an estimated five million victims in the United States alone.

SUMMARY

In one aspect, an implantable pump system for assisting blood flow in a patient includes a blood flow path comprising a flexible conduit, at least one valve in fluid connection with the flexible conduit, a drive system in operative connection with the valve to move the valve in a reciprocating manner, an implantable control system and at least one sensor in communicative connection with the control system. The sensor is adapted to measure at least one property of blood. The control system is adapted to control movement of the valve on the basis of data regarding position of the valve with respect to time or a derivative thereof (that is, position, velocity, acceleration or a derivative thereof) in combination with data of the measured at least one property of blood from the sensor.

The implanted control system may, for example, be adapted to be in communicative connection with an external system to provide data to a caregiver. In a number of embodiments, the implanted control system receives communication from the external system to adjust at least one parameter of pump system control based on data from the at least one sensor.

The measured blood property may, for example, be at least one of blood flow rate or blood pressure. In the case that blood flow rate is measured, the control system may, for example, integrate the blood flow rate during a systolic period to compute stroke volume or the control system integrates stroke volumes over a period of time to compute cardiac output.

In a number of embodiments, the control system includes a heart pacemaker to control heart rate to achieve a determined level of blood flow assist.

In a number of embodiments, the control system is adapted to provide blood flow assist primarily during at least one of an isovolumic contraction period or a latter half of systole. A P wave of an electrocardiogram may, for example, be sensed and used to time operation of the moving valve In a number of embodiments, the degree of pump assist is determined based on the unassisted cardiac output and the incremental level of cardiac output desired by the caregiver to return the patient to a predetermined cardiac output condition. The degree of pump assist may, for example, be controlled or determined by a number of valve assist cycles and/or the frequency of the valve assist cycles.

In a number of embodiments, a measured pressure between the heart and the moving valve pump is used to control the level of valve assist.

The implantable pump system may, for example, further include an implanted communication system in communicative connection with the control system. The implanted communication system may be adapted to transmit information from the at least one sensor to an external system and to receive information transmitted wirelessly from the external system. The control system being adapted to control operation of the pump system as a result of information transmitted from the external system.

In another aspect, a system for assisting blood flow in a patient includes an implantable pump system for assisting in blood flow from the heart. The pump system includes at least one sensor in operative connection with a blood flow path of the pump system to measure at least one property of blood. The sensor is adapted to measure the at least one property of blood when flowing through the pump system during blood flow assist and absent blood flow assist. The system further includes an implantable control system for communicative connection with the implantable pump. The implantable control system may be in communicative connection with at least one external system that is external to the body to provide data to the external system. The external system may be adapted to provide the data to a caregiver. The control system may be adapted to control the pump system based at least in part on data from the sensor.

The at least one sensor may, for example, be a flow sensor in operative connection with the blood flow path to measure a rate of flow of blood through the blood flow path or a pressure sensor in operative connection with the blood flow path to measure pressure blood through the blood flow path. In a number of embodiments, the at least one sensor includes a flow sensor and the pump further includes a pressure sensor in operative connection with the blood flow path.

In a number of embodiments the pump system is a moving valve pump system including a valve assembly which is movable within the blood flow path of the pump. The at least one sensor may, for example, be adapted to measure at least one property of blood when the valve assembly is not being moved and is in an open state so that blood from the heart can flow therethrough to provide data during unassisted blood flow from the heart and may be adapted to measure at least one property of blood when the valve assembly is being moved to provide data during assisted blood flow.

The control system may, for example, be adapted to receive information from the external system to adjust at least one parameter of pump system control. In a number of embodiments, the control system is adapted to receive communications from the external system to adjust at least on parameter of pump system control based on data from the at least one sensor. The external system may, for example, be in wireless communication with the control system.

In a number of embodiments, the control system includes a pacemaker system that is operative to control heart rate to achieve a determined level of blood flow assist. The control system may, for example, be adapted to increase heart rate via the pacemaker. In a number of embodiments, the control system is adapted to increase heart rate to a rate at least 20 percent higher than a normal heart rate for the patient. The increase in heart rate may, for example, be in the range of 20 to 50 percent higher than a normal heart rate for the patient.

In a number of embodiments, the control system is adapted to move the valve only during at least one of an isovolumic contraction period or a latter half of systole. Outflow of blood from the left ventricle of the heart measured by a flow sensor may, for example, be used to time beginning of forward movement of the valve assembly.

In embodiments including a flow sensor, output from the flow sensor may, for example, be integrated over time to compute a stroke volume of blood coming from the left ventricle. Output from the flow sensor may, for example, be integrated over a single systolic time period to compute a stroke volume of blood coming from the left ventricle for a heartbeat. A plurality of stroke volumes may be accumulated over a one period of time to compute cardiac output coming from the left ventricle. A level of pump assist may, for example, be determined based upon a determined or target cardiac output coming from the left ventricle and an incremental cardiac output to return the patient to a determined cardiac output level. The level of pump assist may, for example, be achieved by adjusting one of the number of valve assembly cycles per heartbeat or the frequency of valve assembly cycles.

In a number of embodiments, measured pressure between the valve assembly and the heart is used to control movement of the valve assembly.

In embodiments including a pressure sensor, the pressure sensor may, for example, be in fluid communication with the blood flow path rearward of a rearwardmost position of the valve assembly with respect to the direction of blood through the blood flow path from the heart.

The system may further include at least one sensor adapted to measure a pump system parameter such as at least one of motor current, motor commutation, motor speed, timing, valve assembly speed, valve assembly position, valve assembly acceleration, or a derivative of one of such variables. Pressure rearward of the valve assembly may, for example, be used in combination with pressure on valve assembly during motion thereof to estimate the blood pressure forward of the valve assembly with regard to blood flow from the heart. Pressure on the valve assembly during motion thereof may, for example, be derived from measured motor current.

In a number of embodiments, the system further includes an implantable P wave sensor in communication with the control system to sense an electrocardiographic P wave. The P wave is used to time movement of the valve assembly. The P wave sensor may include a lead adapted to be placed adjacent to a wall of an atrium of the heart. A determined delay from the P wave may, for example, be programmed to initiate movement of the valve assembly (for example, during the isovolumic contraction phase).

In another aspect, a system for assisting blood flow in a patient includes an implantable pump system for assisting in blood flow from the heart and an implantable control system for communicative connection with the implantable pump system. The control system includes a pacemaker system that is operative to control heart rate and the pump system interdependently to achieve a determined level of blood flow assist. As described above, the pacemaker may be adapted to increase heart rate (for example, to increase heart rate to a rate at least 20 higher than a normal heart rate for the patient). In a number of embodiments, the pump system is a moving valve pump system including a valve assembly which is movable within the blood flow path of the pump system. In a number of embodiments, the control system is adapted to communicate with at least one external system that is external to the body to provide data thereto and is adapted to receive information from the external system to alter control of the pump system.

In another aspect, a method of controlling an implantable pump system for assisting in blood flow from the heart, wherein the pump system includes an implantable control system for communicative connection with the implantable pump system, includes providing at one sensor in operative connection with a blood flow path of the pump system to measure at least one property of blood. Control of the implantable pump system is based at least in part on the measured property of blood. The method further includes measuring the at least one property of blood flowing through the pump system during blood flow assist and absent blood flow assist.

The communication system may be adapted to communicate with at least one external system that is external to the body to provide data including data from the first sensor. In a number of embodiments, the sensor is adapted to measure a parameter related to at least one of flow rate or pressure. The pump system may, for example include at least one of a flow sensor in operative connection with the blood flow path to measure a rate of flow of blood through the blood flow path. The pump system may include at least one pressure sensor in operative connection with the blood flow path to measure pressure of blood through the blood flow path.

The pump system may, for example, be a moving valve pump system including a valve assembly which is movable within the blood flow path of the pump system and the at least one sensor is placed in operative connection with the blood flow path. The at least one sensor may, for example, be adapted to measure at least one property of blood when the valve assembly is not being moved and is in an open state so that blood from the heart can flow therethrough to provide data during unassisted blood flow from the heart and may also be adapted to measure at least one property of blood when the valve assembly is being moved to provide data during assisted blood flow.

The method may further include communicating information from the external system to the control system to adjust at least one parameter of pump system control.

In a number of embodiments, the method further includes providing a pacemaker system in operative connection with the control system. The pacemaker system is operative to control heart rate to achieve a determined level of blood flow assist. The method may further include increasing heart rate via the pacemaker system (for example, to a rate at least 20 percent higher than a normal heart rate for the patient).

In a number of embodiments, the control system is adapted to move the valve only during at least one of an isovolumic contraction period or a latter half of systole. Measured outflow of blood from the left ventricle of the heart may, for example, be used to time beginning of forward movement of the valve assembly.

In a number of embodiments in which the at least one sensor includes a flow sensor, output from the flow sensor may, for example, be integrated over time to compute a stroke volume of blood coming from the left ventricle. Output form the flow sensor may be integrated over a single systolic time period to compute a stroke volume of blood coming from the left ventricle for a heartbeat. A plurality of stroke volumes may be accumulated over a one period of time to compute cardiac output coming from the left ventricle. A level of pump assist may, for example, determined based upon determined cardiac output coming from the left ventricle and an incremental cardiac output determined to return the patient to a determined cardiac output level. The level of pump assist may, for example, be adjusted by adjusting one of the number of valve assembly cycles per heartbeat or the frequency of valve assembly cycles.

Measured pressure between the valve assembly and the heart may be used to control movement of the valve assembly. In a number of embodiments, a pressure sensor is in fluid communication with the blood flow path rearward of a rearwardmost position of the valve assembly with respect to the direction of blood through the blood flow path from the heart. The method may further include providing at least one sensor adapted to measure at least one of motor current, motor commutation behavior, motor speed, timing, valve assembly speed, valve assembly position, valve assembly acceleration, or a derivative thereof. Pressure rearward of the valve assembly may, for example, be used in combination with pressure on valve assembly during motion thereof to estimate blood pressure forward of the valve assembly with regard to blood flow from the heart. Pressure on the valve assembly during motion thereof may be derived from measured motor current.

In a number of embodiments, the method further includes providing an implantable P wave sensor in communication with the control system to sense a electrocardiographic P wave and the P wave is used to time movement of the valve assembly. The P wave sensor may include a lead adapted to be placed adjacent to a wall of an atrium of the heart. A determined delay from the P wave can be programmed to initiate movement of the valve assembly during the isovolumic contraction phase.

The control system may, for example, be adapted to control the pump system based at least in part on data from the sensor. Such data may, for example, be provided to a caregiver via an external system in communication with the control system of the pump system to enable the caregiver to adjust control of the pump. Such data may also or alternatively be used in closed loop control of the pump system.

In a number of embodiments in which the pump system is a moving valve pump system including a valve having at least one closure member movable between a closed position and a range of open positions, the closure member may, for example, be biased in an open position. Moreover, the state or position of the closure member (between a closed state and a range of open states) may be actively controlled.

In another aspect, a method of assisting blood flow, includes placing a pump system in fluid connection with the heart, providing a control system for communicative connection with the pump, the control system including a pacemaker system, and pacing the heart in connection with control of pump system to achieve a determined level of blood flow assist. Blood flow may, for example, be assisted in a patient having heart failure with preserved ejection fraction. The pacemaker may, for example, be adapted to increase heart rate. In a number of embodiments, the pacemaker is adapted to increase heart rate to a rate at least 20 percent higher than a normal or natural heart rate for the patient (for example, under the present conditions of the patient). As described above, the pump system may, for example, be a moving valve pump including a valve assembly which is movable within the blood flow path of the pump system.

The control system may, for example, be adapted to communicate with at least one external system that is external to the body to provide data thereto and to receive information from the external system to alter control of the pump system. The method may further include providing at least one sensor in operative connection with the blood flow path of the pump system to measure at least one property of blood. Control of the pump system may, for example, be based at least in part on the measured property of blood. The at least one property of blood flowing through the pump system may, for example, be measured during blood flow assist and absent blood flow assist.

In another aspect, a pump system for assisting blood flow in a patient includes a blood flow path including a flexible conduit (for example, adapted to be placed in series with and/or in line with a blood vessel such as the aorta or the ascending aorta), at least one valve in fluid connection with the flexible conduit, a drive system in operative connection with the valve to move the valve in a reciprocating manner, a control system in operative connection with the drive system, and a pressure sensor in communicative connection with the control system and in fluid connection with the blood flow path. The control system may, for example, be operative to decrease a level of assist if the pressure sensor measures a pressure below a determined or threshold value. The measured pressure is measured during movement of the valve for comparison to the determined value.

In another aspect, a pump system for assisting blood flow in a patient includes a blood flow path comprising a flexible conduit (for example, adapted to be placed in series with and/or in line with a blood vessel such as the aorta or the ascending aorta), at least one valve in fluid connection with the flexible conduit, a drive system in operative connection with the valve to move the valve in a reciprocating manner; and a control system in operative connection with the drive system. The control system is adapted to receive a signal of rhythm of the heart. The control system is further adapted to begin movement of the valve via the drive system during the isovolumic contraction phase. A P wave may, for example, be used to time beginning of movement of the valve during the isovolumic contraction phase.

In a further aspect, a pump system for assisting blood flow in a patient includes a blood flow path including a flexible conduit (for example, adapted to be placed in series with and/or in line with a blood vessel such as the aorta or the ascending aorta), at least one valve in fluid connection with the flexible conduit, a drive system in operative connection with the valve to move the valve in a reciprocating manner, a control system in operative connection with the drive system, and a flow sensor in communicative connection with the control system and in fluid connection with the blood flow path. Data of increasing blood flow from the heart occurring early in systole is sensed by the flow sensor and transmitted to the control system. The control system is adapted to time initiation of movement of the valve by the drive system at least in part on the basis of the data.

In still a further aspect, a system for assisting blood flow in a patient includes an implanted pump system including an implanted control system in operative connection with the pump system, a sensor system adapted to measure at least one of a parameter of pump system operation or of blood, and an implanted communication system in communicative connection with the control system. The implanted communication system is adapted to transmit information from the sensor system wirelessly to an external system and to receive information transmitted wirelessly from the external system. The control system is adapted to control operation of the pump system as a result of information transmitted from the external system. The external system may, for example, be adapted to provide information to a caregiver. The external system may, for example, be adapted create information to be transmitted to the implanted controller on the basis of input from the caregiver.

In a number of embodiments of the system, the pump system includes a blood flow path comprising a flexible conduit (for example, adapted to be placed in series with and/or in line with a blood vessel such as the aorta or the ascending aorta), at least one valve in fluid connection with the flexible conduit, and a drive system in operative connection with the valve and with the control system, wherein the drive system is adapted to move the valve in a reciprocating manner. The pump system can include at least one of a flow sensor in communicative connection with the control system and in fluid connection with a blood flow path of the pump system or pressure sensor in communicative connection with the control system and in fluid connection with a blood flow path of the pump system.

In a number of embodiments, the system further includes a pacemaker system in operative connection with the control system. The control system may, for example, be adapted to control heart rate via the pacemaker system in combination with control of the pump system to achieve a determine level of assist.

In a number of embodiments, the drive system includes a rotary motor, a speed reducing system in operative connection with the rotary motor and a convertor operatively connected to the speed reducing system. The converter is operatively connected to the valve to drive the valve in a reciprocating manner. In a number of embodiments, the speed reducer includes a spur gear driving a ring gear, wherein the converter is operatively connected to the speed reducer. The ring gear may, for example, be in operative connection with the converter. In a number of embodiments, the converter includes an eccentric member extending from the ring gear. In a number of embodiments, the converter further includes a rotating element connected to the eccentric member that engages a cam member operatively connected to the valve to drive the valve in a reciprocating, linear manner.

The flexible conduit of the blood flow path may be positioned within a sealed housing. A volume between the flexible conduit and housing may, for example, be filled with an aqueous fluid having dissolved solutes to provide an osmolarity approximately equal to the osmolarity of blood. The fluid may, for example, be an aqueous salt solution. The drive system may, for example, be in fluid connection with the volume, and the fluid may be present within the drive system. In a number of embodiments, the fluid is adapted to dissipate heat from the drive system. The fluid may, for example, include at least one hydrophilic lubricant.

In a number of embodiments, the projected average life of pump systems hereof is intended to be that of current heart transplants, namely approximately 10 years.

The technology described herein, along with the attributes and attendant advantages thereof, will best be appreciated and understood in view of the following detailed description taken in conjunction with the accompanying drawings.

BRIEF DESCRIPTION OF THE DRAWINGS

FIG. 3A illustrates a front view of the pump system of FIG. 2 with closure members of the valve assembly of the pump system in a partially open state.

FIG. 3B illustrates a perspective view of the pump system of FIG. 2.

FIG. 3C illustrates a side view of the pump system of FIG. 2.

FIG. 4A illustrates another side view of the pump system of FIG. 2.

FIG. 4B illustrates a cross-sectional view of the pump system of FIG. 2 along section A-A of FIG. 4A wherein the valve closure members are in a closed state.

FIG. 4C illustrates a cross-sectional view of the pump system of FIG. 2 along section A-A of FIG. 4A wherein the valve closure members are in an open state.

FIG. 5A illustrates a side view of an embodiment of a shaft for a rotary motor for used in pump system hereof in operative connection with a rolling element bearing.

FIG. 5B illustrates a rear view of the shaft and bearing assembly of FIG. 5A.

FIG. 5C illustrates a cross-sectional view of the shaft and bearing assembly of FIG. 5A along section D-D of FIG. 5A.

FIG. 5D illustrates a rear perspective view of the shaft and bearing assembly of FIG. 5A.

FIG. 5E illustrates a perspective cutaway view of the shaft and bearing assembly of FIG. 5A wherein the assembly is cut along section D-D of FIG. 5A.

FIG. 5F illustrates a perspective, exploded or disassembled view of the shaft and bearing assembly of FIG. 5A.

FIG. 6C illustrates a perspective view of the flow conduit assembly and curved connector of the pump system of FIG. 2 (with the housing section of the flow conduit removed) and an embodiment of a converter for converting rotary motion to reciprocating motion.

FIG. 6D illustrates a perspective view of the flow conduit assembly and curved connector of the pump system of FIG. 2 (with the housing section of the flow conduit removed) and another embodiment of a converter for converting rotary motion to reciprocating motion.

FIG. 6E illustrates a perspective view of an embodiment of a race member and roller elements thereof for used in a linear bearing.

FIG. 7A illustrates a perspective view of an embodiment of a linear rolling element bearing for use in the pump systems hereof.

FIG. 7B illustrates a top view of the linear rolling element bearing of FIG. 7A.

FIG. 7C illustrates a side view of the linear rolling element bearing of FIG. 7A.

FIG. 7D illustrates a front view of the linear rolling element bearing of FIG. 7A.

FIG. 7E illustrates several geared roller elements suitable for use in the linear rolling element bearing of FIG. 7A.

FIG. 8F illustrates a perspective exploded or disassembled view and a perspective assembled view of the seal of FIG. 8D.

FIG. 8G illustrates a side cutaway view of the seal of FIG. 8D installed in a sleeve or sheath which can be placed in sealed connection with the valve assembly.

FIG. 8H illustrates a top plan view an embodiment of the seal of FIG. 8D installed in the sleeve or sheath of FIG. 8G.

FIG. 8K illustrates a top view of the valve assembly of FIG. 8A wherein an upper closure of a linear rolling element bearing in operative connection with the rack of the activating system is removed and wherein the closure member thereof in an open position FIG. 8L illustrates a perspective view of the valve assembly of FIG. 8A wherein an upper closure of a linear rolling element bearing in operative connection with the rack of the activating system is removed and wherein the closure member thereof in an open position.

FIG. 8M illustrates a front view of the valve assembly of FIG. 8A with the closure member thereof in an open position.

FIG. 8N illustrates a side view of the valve assembly of FIG. 8A with the closure member thereof in an open position.

FIG. 9A illustrates a perspective view of a base member of an embodiment of a closure member hereof.

FIG. 9B illustrates an enlarged top view of a closure member including the base member FIG. 9A and a layer of a blood compatible, flexible material over and adjacent the base member.

FIG. 9C illustrates a front view of the closure member of FIG. 9B, illustrating the extension of the flexible material past the edges of the base member.

FIG. 9D illustrates a side view of the closure member of FIG. 9B.

FIG. 9E illustrates a rear view of the closure member of FIG. 9B.

FIG. 11C illustrates the effect of moving a moving valve during the isovolumic contraction (one valve stroke) and during the latter half of systole (two valve strokes) upon blood flow.

DETAILED DESCRIPTION

Figure 1:
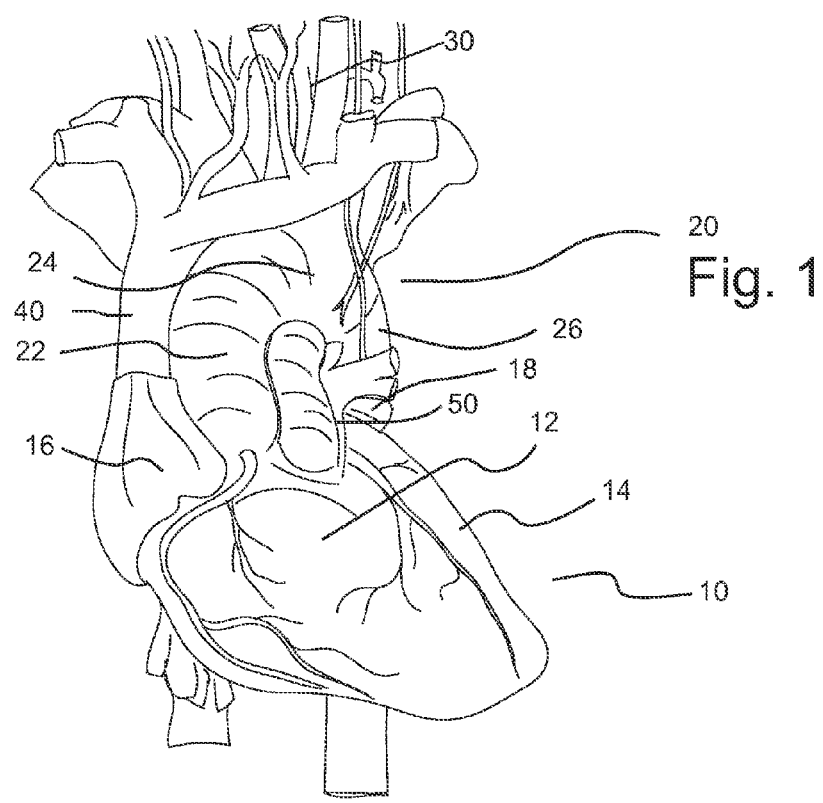
FIG. 1 illustrates a perspective view of the human heart including some of the surrounding vasculature and some of the surrounding organ structure.

As used herein and in the appended claims, the singular forms "a," "an", and "the" include plural references unless the content clearly dictates otherwise. Thus, for example, reference to "a valve assembly" includes a plurality of such valve assemblies and equivalents thereof known to those skilled in the art, and so forth, and reference to "the valve assembly" is a reference to one or more such valve assemblies and equivalents thereof known to those skilled in the art, and so forth.

In a number of embodiments hereof devices, systems and methods are disclosed for assisting blood flow using a moving (for example, oscillating) valve assembly or a plurality of such valve assemblies to propel blood. Pump systems hereof can be fully implanted or temporarily connected to the circulation using percutaneous blood conduits. Pump systems hereof can, for example, be fully or completely implanted for a period of months to years to alleviate or correct heart failure and related symptoms.

Inline moving valve pumps located in the space normally occupied by, for example, the ascending human aorta have been proposed in which a linear motor actuates valve movement. As used herein, the terms "in line or "inline" when used in connection with the position of a pump system hereof within the body refers to a moving valve pump in which the flow path of blood through the pump is in series with a blood vessel (for example, the aorta or the ascending aorta) and the path of the moving valve passes through at least a portion of the volume occupied by the blood vessel (for example, the ascending aorta) prior to implantation of the moving valve pump. Because of the critical organs surrounding the ascending human aorta, there is very limited space for a valve drive mechanism. A compact linear motor was previously believed to be required for use in the limited space around the aorta. Moreover, the ascending aorta is typically three inches or less in length (approximately two inches in length for an average adult), which is a very short distance for the provision of a flow conduit assembly of an inline moving valve pump system (for example, including one or more flexible conduits, sealing end rings, and blood tight aortic connections at each end of the pump system). The present inventors have discovered that suitably sized linear motors have inadequate output power for driving a moving valve pump at motor temperatures reasonably suitable for implantation in the human body, and, for example, to be in series with and/or in line with a blood vessel such as the aorta (for example, the ascending aorta).

Rotary motors have the advantage of higher power compared to an equally sized linear motor. However, implantable rotary motors for an inline moving valve pump would have to be placed in the vicinity of the aorta, consuming organ space. In a number of embodiments hereof, pump systems having a drive system including a rotary motor and a converter (to convert the rotary motion of the rotary motor to the desired reciprocating motion of the moving valve) exhibit sufficient driving power for the moving valve with acceptable heat emission. A rotary-to-linear drive or converter can be used for reciprocating, linear valve motion, or a rotary-to-curvilinear drive or convertor can be used for reciprocating, curvilinear valve motion. A speed reduction system or speed reducer can, for example, be provided between the rotary motor and the converter. Such a speed reduction system can, for example, be used to decrease the size (volume) of the rotary motor required. Representative embodiments of pump systems hereof exhibit a form factor that does not significantly interfere with the function of the critical organs surrounding, for example, the aorta.

Review of the physics describing motor power illustrates the power output advantages of a rotary motor compared to a linear motor, and particularly, a rotary motor including a speed reducer. Output power is the product of torque and rotational speed for a rotary motor, while power is the product of force and velocity in the case of a linear motor. Electromagnetically induced force, expressed in Newtons, is the product of magnetic field strength expressed in Tesla, the length of an electric conductor in meters, and the current flowing in the conductor expressed in amperes, provided the current is flowing perpendicular to the magnetic flux lines. If one assumes an equal volume of copper for carrying current and a rare earth magnet material such as neodymium, for establishing magnetic field strength, equally sized linear and rotary motors will be capable of creating roughly the same amount of electromagnetic force. However, the generated power will be the product of this force and the corresponding velocities. A linear motor, directly linked with a valve might, for example, move the valve 0.015 meters (1.5 centimeters) in 50 milliseconds for a velocity of approximately 0.3 meters per second. A rotary motor linked to the valve through, for example, a 5× speed reducer, and a rotary-to-linear converter (for example, including a cam element), and having a rotor diameter of 0.02 meters (2 centimeters), will have rotor surface motion per valve stroke of (pi radians×0.01 meters/radian×5)/0.05 or 3.14 meters per second. In this representative example, the rotary motor thus provides more than ten times the velocity of the linear motor. Therefore, for an equivalent mass and size of linear and rotary motors, the rotary motor can be expected to produce roughly ten times the output power compared with the same input power. The substantial difference in power generation efficiency allows use of a suitably small rotary motor, especially when coupled with a speed reducer to perform the required work of a moving valve pump located in the limited space of the ascending aorta, with acceptable heat generation. A linear motor suitable to perform the same amount of work would have to be too large and/or would emit too much heat.

FIG. 1 illustrates a frontal view of human heart 10, including some of the surrounding vasculature and other surrounding organ structures. FIG. 1 does not show the bony thorax, including the sternum and attached ribs, that limit the space immediately in front of heart 10 and associated structures. Heart 10 includes right ventricle 12 and left ventricle 14. As described above, left ventricle 14 is the main pumping chamber of heart 10. During left ventricular contraction or systole, blood is pushed through the aortic valve into ascending aorta 22, which is the main artery leading to the body. In the vicinity of heart 10, aorta 20 includes the ascending aorta 22, the arch of aorta or aortic arch 24 and the descending aorta 26. For placement of a pump system in line with ascending aorta 22, critical peri-aortic structures include, but are not limited to, right atrium 16 and left atrium 18, esophagus 30, superior vena cava 40, the pulmonary veins (not shown) and pulmonary artery 50. Left ventricle 14 normally has a conical form, the long axis of which is generally in line with the root of ascending aorta 22. Pulmonary artery 50 and the right branch thereof, wrap around and behind ascending aorta 22. Right atrium 16, or entrance chamber to right ventricle 12, bounds the lower portion of ascending aorta 22 on its right side (with reference to the orientation of patient 5). In the illustration of FIG. 1, superior vena cava 40 bounds the higher portion of ascending aorta 22 to its right (with reference to orientation of patient 5).

Figure 2:
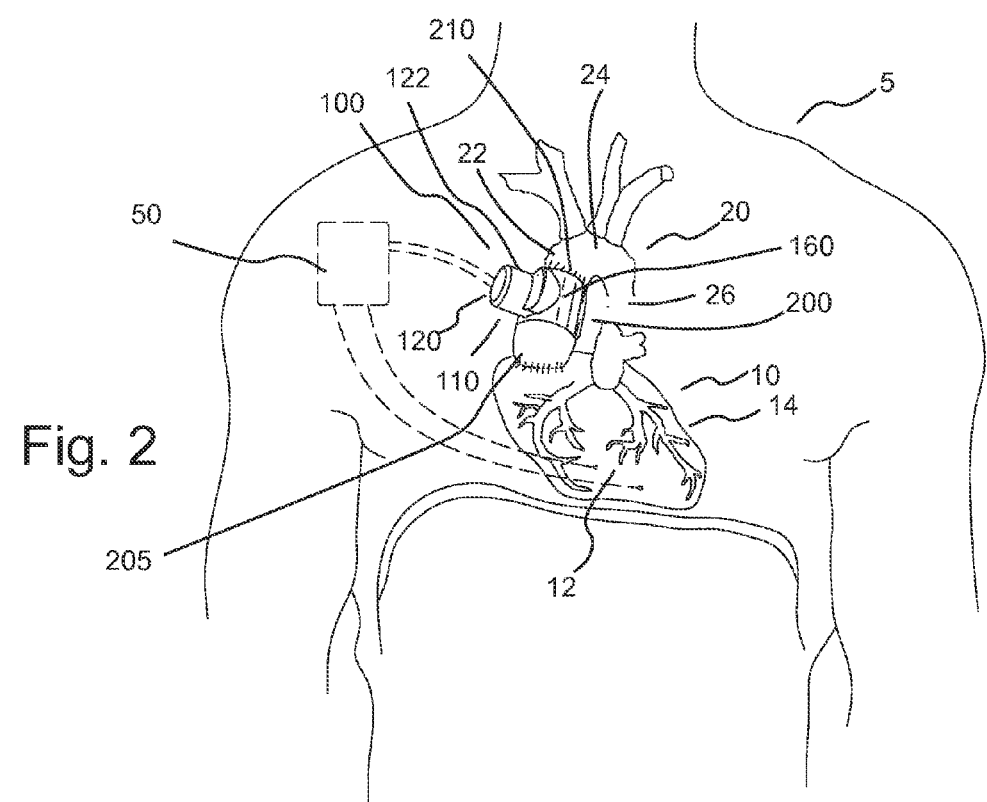
FIG. 2 illustrates a perspective view of an embodiment of a pump system hereof placed in line with the ascending aorta.

FIG. 2 illustrates an embodiment of an inline pump system 100 hereof wherein a blood flow path of pump system 100 is placed in line with ascending aorta 22. Some of the vasculature and structures surrounding the heart illustrated in FIG. 1 are removed in FIG. 2. Because of the bony thorax, limiting the space in front of heart 10 as illustrated in FIGS. 1 and 2, drive system 110 of pump system 100, including rotary motor 120 and connected speed reducer 160 in the illustrated embodiment (see, for example, FIGS. 3A through 3C), protrude sideways at a right anterior oblique angle (with reference to the orientation of patient 5) from conduit assembly 200 through which blood flows, which is a generally cylindrical structure over a portion thereof. In the frontal view of FIG. 2, rotary motor 120 protrudes to the left (of the viewer of FIG. 2, opposite the reference with respect the orientation of patient 5) of the upper end of ascending aorta 22 to avoid interfering with the bony thorax and vital surrounding structures. With respect to critical peri-aortic structures, there is suitable space for pump system 100 at the upper end of ascending aorta 22 and toward the right lung (not shown), where the right lung is in close proximity to ascending aorta 22. This right lung space can be occupied by the protruding portion of drive system 110 without significant health consequences or significant spatial interference with other vital structures. In the illustrated orientation, drive system 110 can be sufficiently small in volume to displace only a small amount of volume of the right lung and sufficiently short in axial length to not interfere with the inner surface of the bony sternum that bounds this peri-aortic space anteriorly.

FIG. 2 illustrates schematically a control system 50 in operative connection with pump system 100. Control system 50 can, for example, be implanted subcutaneously at a position remote from pump system 100 in the upper chest of the patient and placed in communicative connection with pump system 100 (for example, via wiring). Control system 100 includes control algorithms for valve movement of pump system 100, and can, for example, include a microprocessor-based position servo control system. Heart rhythm can, for example, be used to time the valve oscillations. In FIG. 2, leads to heart 10 provide a signal of the heart's rhythm to control system 50.

FIGS. 3A through 4C illustrate moving valve pump system 100 in various orientations. As described above, flow conduit assembly 200 can be generally cylindrical in shape. Rotary motor 120 and speed reducer 160 can also be generally cylindrical in shape. In a number of embodiments of pump systems hereof, a housing or housing section of the flow conduit assembly is adjacent to and extends at an angle from a housing or housing section of the drive system. The housing sections can be formed separately and connected or formed as an integral or monolithic housing or case. In a number of embodiments, the axis of the rotary motor (see axis $A_2$ in FIGS. 4D and 4F) within the housing section for the drive system extends to intersect the housing of the flow conduit assembly. In the embodiment of FIGS. 3A through 4C, a housing section 122 of drive system 110 extends generally perpendicular to a housing section 210 of flow conduit assembly 200. Axis $A_2$ of shaft 128 of rotary motor 120 extends generally perpendicular to axis $A_1$ of flow conduit assembly 200 (which is also the axis or centerline of blood flow through flow conduit assembly 200 in the illustrated embodiment). The conformations or form factors described above assist in reducing or minimizing the volume of the pump system and in reducing, minimizing or eliminating interference with vascular structure and organ structure in the vicinity of aorta 20.

The total volume displaced by the pump system can, for example, be less than 400 cc, less than 200 cc or even less than 180 cc. The volume of flow conduit assembly 200 and the extending housing section of the drive system may, for example, be less than 300 cc, less than 200 cc or even less than 120 cc. The volume displaced by the extending housing section of the drive system may, for example, be less than 150 cc, less than 100 cc or even less than 50 cc. A distance $D_1$ (see FIG. 4C) from axis $A_1$ (or the centerline of blood flow) to a distal end of the housing section for the drive system (housing section 122 in the embodiment illustrated in FIGS. 3A through 4C) may, for example, be less than 12 cm, less than 10 cm or even less than 8 cm. A distance $D_2$ (see FIG. 4C) from axis $A_1$ (or the centerline of blood flow) to the position at which the motor shaft exits the body of the motor (typically, at the face of a bearing on an axial end of the motor) may, for example, be less than 6 cm or less than 4 cm. A distance or length $D_3$ (see FIG. 4C) corresponding to the length of flow conduit assembly 200 (through which a valve assembly 300 moves in a reciprocating manner) extends can, for example, be less than 7.6 cm, less than 6.4 cm or even less than 5 cm.

In one embodiment, the total volume of pump system 100 is approximately 170 cc, the volume of flow conduit assembly housing section 210, a curved connector 205 attached thereto and a suture connector 208 attached thereto is approximately 136 cc; the volume of flow conduit assembly housing section 210 is approximately 79.08 cc; the volume of drive system housing section 122 (encompassing rotary motor 120 and speed reducer 160) is approximately 34 cc; distance $D_1$ is approximately 7.75 cm; and distance $D_3$ is approximately 4.52 cm. In that embodiment, the volume of aorta 20 displaced by pump system 100 is approximately 75 cc (calculated using an average aorta radius of 1.75 cm). The net increase in volume which impinges on non-aortic structures is approximately 95 cc (170 cc-75 cc).

As described above, in the embodiment illustrated, for example, in FIGS. 3A through 4C, drive system 110 (including rotary motor 110 and speed reducer 160 and housing section 122 therefor) is attached generally perpendicular to an axis $A_1$ (see, for example, FIGS. 4A and 4C) of a housing section 210 of conduit assembly 200 through which a valve assembly 300 moves in the direction of axis $A_1$ to assist blood flow. Axis $A_2$ of shaft 128 (see, for example, FIG. 4F) of rotary motor 120 and the axis of ring gear 164 of speed reducer 160 are generally perpendicular to axis $A_1$ of flow conduit assembly 200. As also described above, upon implantation, drive system 110 can be oriented in the right anterior oblique direction into the space normally occupied by the right lung. If drive system 200 was oriented on the anteroposterior axis (that is, aimed straight out of the illustration toward the viewer in FIG. 2), it would interfere with the bony thorax covering heart 10 and ascending aorta 22.

Figure 4H:
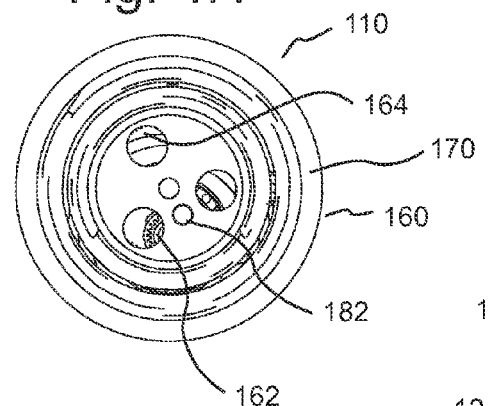
FIG. 4H illustrates a front view of the drive system of FIG. 4D.
Figure 4D:
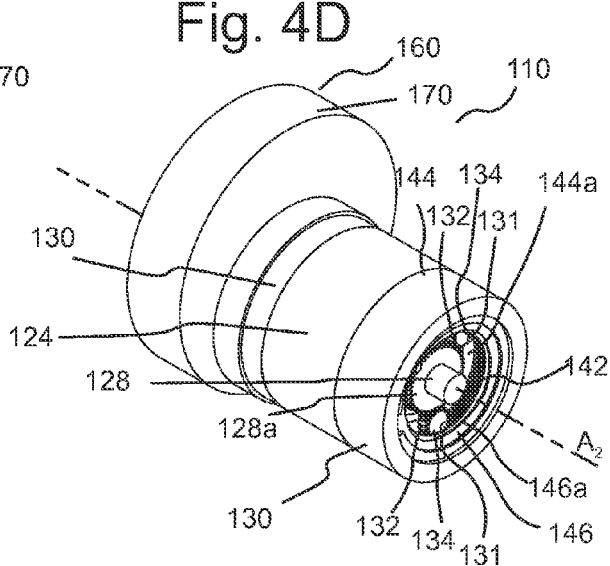
FIG. 4D illustrates an embodiment of a drive system for use in pump systems hereof.
Figure 4E:
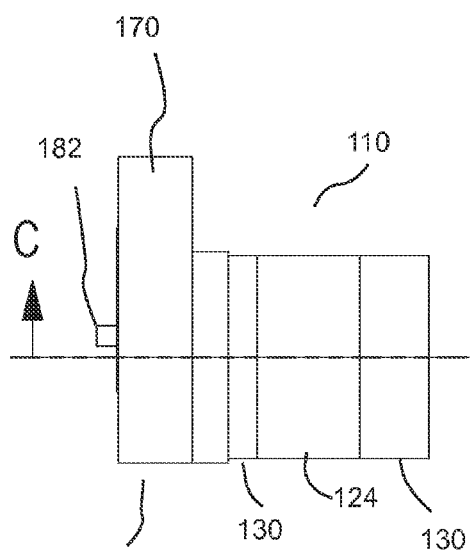
FIG. 4E illustrates a side view of the drive system of FIG. 4D.
Figure 4G:
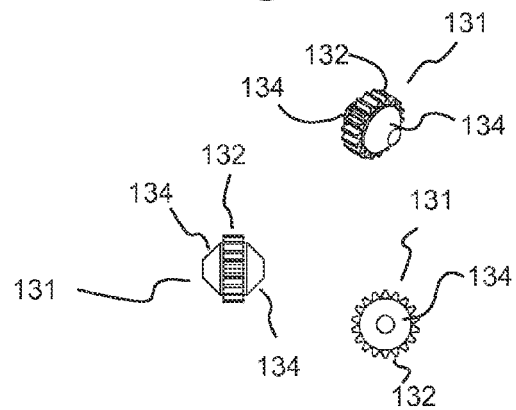
FIG. 4G illustrates several geared roller elements suitable for use in rolling element bearing of the drive system of FIG. 4D in various orientations.
Figure 4F:
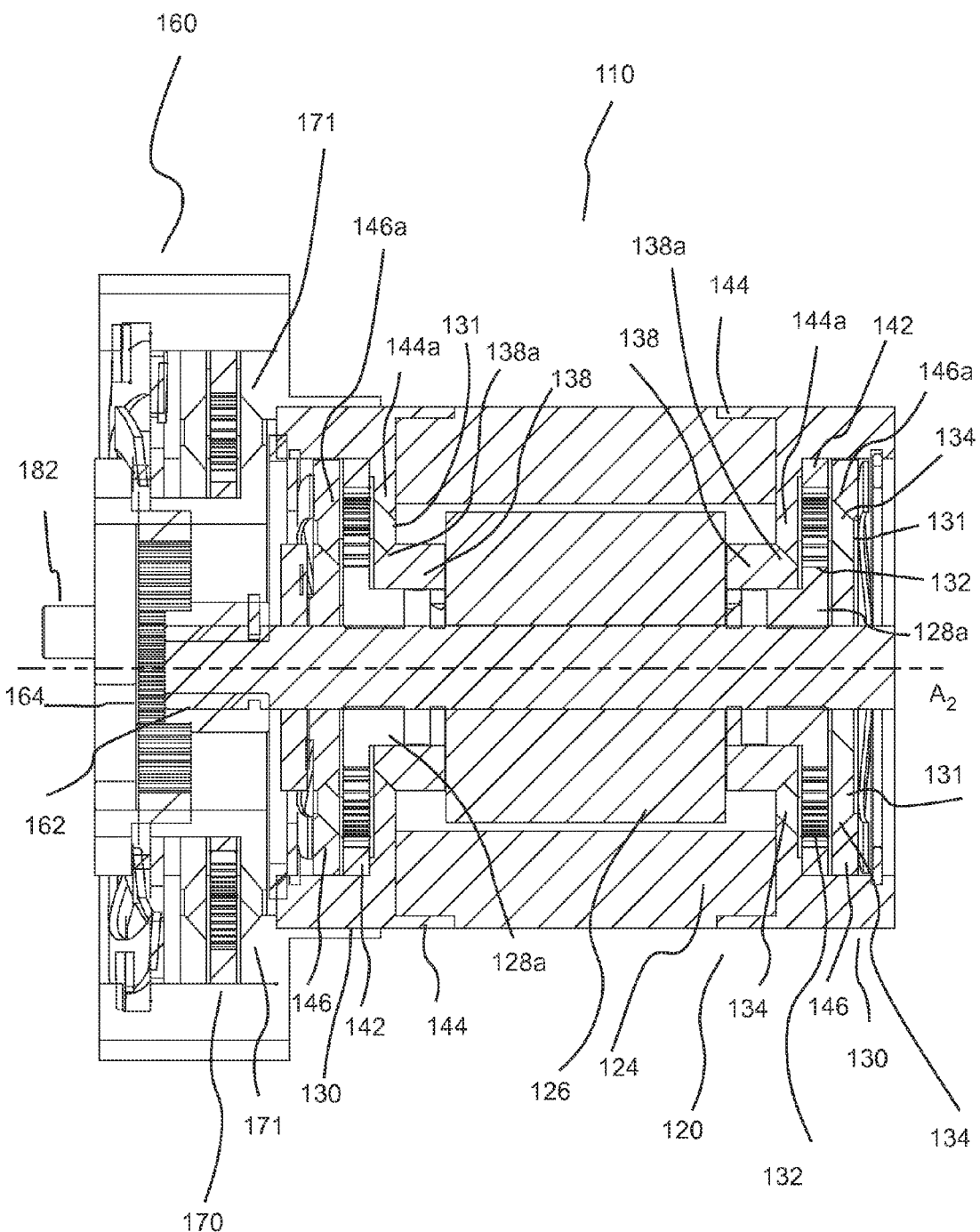
FIG. 4F illustrates a cross sectional view of the drive system of FIG. 4D along section C-C.

FIGS. 4B and 4C illustrate cross-sectional views of moving valve pump system 100. Rotary motor 120 can, for example, be a brushless direct current motor positioned within housing section 122 (which can be generally cylindrical over at least a portion thereof). A stator 124 of rotary motor 120, as its name implies, is stationary and physically connected to mechanical ground. As used herein, the term "mechanical ground" refers to a non-moving portion of a system or subsystem being discussed. As known in the motor arts, stator 124 can, for example, include a series of electromagnets arranged in a continuous circle that are electronically activated in a carefully timed sequence to rotate a rotor 126. Rotor 126 can, for example, include rare earth magnets located on its periphery that interact with electromagnets of stator 124 to produce the torque force necessary to rotate rotor 126. As described further below, shaft 128 (see, for example, FIG. 4F) of rotor 126, and consequently rotor 126, can, for example, be suspended or positioned within motor housing 122 by rolling element bearings 130.

In the illustrated embodiment, speed reducer or speed reduction system 160 is in operative connection with rotor shaft 128. In FIGS. 4A through 4C, housing 122 houses both the components of rotary motor 120 and speed reducer 140. As described above, housing section 122 can be attached to housing section 210 or formed at least partially integrally or monolithically therewith to form a housing or case for pump system 100.

In the illustrated embodiment, speed reducer 160 includes a spur gear or a pinion gear 162 attached to rotor shaft 128. Spur gear 162 engages and rotates a ring gear 164. Ring gear is suspended or positioned by a bearing such as a rolling element bearing 170 including roller elements 171 as described below in connection with rolling element bearings 130 of rotary motor 120. The combination of spur gear 162 and ring gear 164, provide a number of advantages over, for example, a planetary speed reducer because of the need for bushings or bearings for each planet gear of the planetary speed reducer and the additional need for a power takeoff from the centers of each of the planets thereof. Using spur gear 162 to drive ring gear 164 is much simpler, and requires only two gears for achieving a suitable speed reduction. In the illustrated embodiment, speed reducer 160 is operatively connected to a rotary-to-linear converter 180 (see, for example, FIGS. 6A through 6E). Rotary-to-linear converter 180 is operatively connected to valve assembly 300 to drive valve assembly 300 in a linear reciprocating manner by converting the rotating motion of ring gear 164 to linear, reciprocating motion.

As described above, speed reducer 160 can be eliminated in the case of certain rotary motors. In such an embodiment, the rotary motor would be connected directly to the converter to convert rotary motion to the reciprocating motion of the valve assembly. However, a rotary motor providing sufficient torque at lower speeds would be required. Such a rotary motor would have a substantially increased volume and weight as compared to a rotary motor suitable for use in connection with a speed reducer.

The magnitude of the lifetime requirements for a moving valve pump which is intended to be an alternative to a heart transplant is substantial. Although, heart transplants are very effective solutions for severe heart failure, heart transplants are limited by availability of suitable donor hearts (approximately 2,400 per year in the US). The need for a heart transplant equivalent replacement pump is therefore great. However, the desired lifetime for a pump system equivalent to a heart transplant is on the order of ten years of very reliable operation. If a moving valve pump system such as pump system 100 averages three cycles/forward strokes per heartbeat, and the average heart rate of a pump recipient patient is 80 beats per minute, 1.26 billion reliable valve cycles are required from the pump system 100 (10 years×365 days/year×24 hours/day×60 minutes/hour×80 heartbeats/minute×3 cycles/heartbeat). This is a high number of cycles for reliable operation of mechanical linkages from rotary motor 120 to valve assembly 300.

Transferring energy from rotary motor 120 to valve assembly 300 with such a long lifetime requirement presents a problem of wear of bearings used in pump system 100. As used herein, a "bearing" refers to a device that allows constrained relative motion between two or more components (most commonly, rotational or linear movement). Bushings, which are independent plain bearings inserted into a housing to provide a bearing surface for rotary or linear applications, can be overly susceptible to wear. In general, sliding or friction bearings are subject to wear and would be expected to decrease pump system lifetime. Rolling element bearings carry a load by placing rolling elements between two race components. The relative motion of the components causes the rolling elements to roll with little resistance. Rolling element bearing can provides improved wear resistance as compared to bushings. A ball bearing is a type of rolling element bearing in which balls maintain separation between the moving parts of the bearing. Because of cost and availability reasons, ball-shaped rolling elements are typically used in motors to link mechanical assemblies. However, ball-shaped rolling elements provide a single point of contact with the moving component(s) of the bearing. Rolling element bearings, which provide a generally linear contact with moving parts (for example, cylindrical rolling elements), exhibit higher load carrying capability and can provide improved wear resistance compared to some ball bearings. A problem with a number of currently available rolling element bearings, given the relatively long lifetime requirements for pump system 100, is the use of cages to maintain proper placement of the rolling elements. Because rubbing between the cage and the rolling elements is unavoidable and generates wear and debris, rolling element bearings which do not include cages (sometimes referred to herein as cageless rolling element bearings) are used in several embodiments hereof. Cageless rolling element bearings can, for example, be provided by using matched or meshing gear teeth on the rolling elements and the cooperating races to properly locate the rolling elements within the rolling element bearing assemblies. Since the respective gear teeth of the rolling elements and races mesh, rubbing is virtually eliminated and bearing life is increased. Additionally, roller element bearings with extending bearing surfaces can be used instead of balls for the rolling elements in at least some of the mechanical linkages of pump systems hereof. As described above, rollers provide greater load bearing capacity compared to balls, which provide only point contact for load bearing. Rolling elements or rollers with extended contact bearing surfaces for use herein can, for example, include angled, tapered, canted or arced extending bearing surfaces to better accommodate bending moments and stresses on the rolling element bearings.

Certain caged rolling element bearings, including ball bearings, may also be suitable for use in at least some of the mechanical linkages of the pump systems hereof. For example, "hybrid" rolling element bearings are available wherein the inner and outer races are formed from a bearing hard steel, while the rolling balls are formed from a ceramic material such as silicon nitride. Hard ceramic balls, formed from silicon nitride are lighter than steel and have a higher modulus of elasticity, which makes them stiffer than steel. Moreover, ceramic balls are smoother than steel balls and do not microscopically weld to the steel races because of the dissimilarities of the materials. Hybrid rolling element bearings including ceramic rolling balls or rollers and durable cages are, for example, available from The Barden Corporation of Danbury, Conn. Durable or long-life cages can, for example, be formed from a thermoplastic material.

Whether the bearings used in the pump systems hereof are caged or cageless, and whether such bearings include balls or rollers with extending bearing surfaces, such bearing can, for example, include shielding. Shielding (for example, a metallic cover or shield) covers the rolling elements and races of shielded bearings. Typically, shielding is used to keep debris from entering the bearing or to retain a lubricant such as grease within the bearing. In the case of bearings used in the pump systems hereof, however, shielding can be used to prevent debris caused by wear of one or more components of the bearing from escaping the bearing. Typically, shielding on both sides of a bearing is desirable.

FIGS. 4D through 4G illustrate drive system 110 wherein rotary motor 120 is slightly different in appearance from rotary motor 120 illustrated in FIGS. 4A through 4C, but drive systems 110 operates in the same manner as described above. The appearance of rotary motor 120 in FIGS. 4A through 4G can, for example, provide a better view of the operation of one embodiment of rolling element bearings used therein (see, for example, FIGS. 4D and 5A through 5F).

As described above, rotor shaft 128 is supported by rolling element bearings 130. In the illustrated embodiment of, for example, in FIG. 4G. rolling elements 131 of rolling element bearings 130 include a gear or toothed section 132 including radiating gear teeth. Rolling elements 131 further include angled or tapered bearing surfaces 134 extending on each lateral side of gear section 132.

Rotary shaft 128 has two relatively larger gear wheels 128*a* keyed or otherwise fixed thereto. The geared teeth of roller elements 131 cooperate with the teeth of gear wheels 128*a*. FIGS. 5A through 5F illustrates several views of shaft 128 of rotary motor 120 with one rolling element bearing 130 in operative connection therewith. To form a radially inward race of bearing 130, a bearing member 138 (see, for example, FIGS. 5C, 5E and 5F) having an angled or tapered bearing surface 138*a* can be positioned on one or both sides of gear wheel 128*a* to provide radially inward surfaces for angled bearing surfaces 134 of roller elements 131 to bear against.

Rotary motor 120 further includes a radially outward positioned race to cooperate with roller elements 131. As illustrated, for example, in FIGS. 4D and 5B through 5F, the radially outward positioned race is formed by an intermediate gear ring 142 including radially inward radiating gear teeth and end rings 144 and 146 which include angled or tapered bearing surfaces 144a and 146a, respectively. End ring 144 also provides a seating for gear ring 142 and end ring 146.

As illustrated, for example, in FIGS. 4D, and 5B through 5F) rolling elements 131 are arranged around gear wheel 128a. Bearing surfaces 138a. 144a and 146a are adapted to support shaft 128 and the elements attached thereto. The intermeshing teeth of gear wheel 128a, roller elements 131 and gear ring 142 operate to prevent relative movement of roller elements 131 about the inner and outer races of rolling element bearing 130, thereby obviating the need for cages in the embodiment of bearing 130.

As illustrated, for example, in FIGS. 4B, 4C, and 6A through 6D, a blood flow path of pump system 100 which includes at least one flexible blood flow conduit 240 (which can, for example, be corrugated or otherwise folded to provide flexibility over at least a portion thereof) can, for example, be placed in line with ascending aorta 122. Blood flows through flow conduit 240 and is driven by moving valve assembly 300 (see, for example, FIGS. 4B, 4C and 6B). Flow conduit 240 is designed and constructed of a flexible material so that it can be extended and compressed along its length as valve assembly 300 moves forward and rearward (for example, in an oscillating manner). Flow conduit 240 can, for example, operate in the manner of a bellows and is sometimes referred to as such herein. Valve assembly 300 can, for example, be attached (for example, by an adhesive) via a peripheral support structure or valve ring 310 thereof to a single flow conduit 240. Alternatively, one flow conduit 240 can be attached to a rearward end of valve support structure 310 and another flow conduit 240 can be attached to a forward end of valve support structure 310. As described above, the walls of the flow conduit 240 can be corrugated, stretchable or otherwise moveable along the path of movement of valve assembly 300 to allow movement (for example, via contraction and expansion) of flow conduit 240 as valve assembly 300 moves in a reciprocating or back-and-forth linear manner. In a number of embodiments, flow conduit 240 is formed from a flexible, durable, bio/blood compatible material such as a metal or a polymeric material which exhibits in vivo biostability over the life of pump system 100. In a number of embodiments wherein flow conduit 240 is formed of a polymeric material, the polymer is a urethane polymer, which can be elastomeric. The conduit wall material of flow conduit 240 can, for example, be BIONATE® urethane polymer, which is a durable implant grade, bio/blood compatible thermoplastic polycarbonate urethane available from Polymer Technology Group, Inc. of Emeryville, Calif. In a number of embodiments, a generally consistent wall thickness is maintained over the length of flow conduit 240 to avoid weak areas in flow conduit 240. For example, in a number of embodiments, flow conduit 240 was formed from BIONATE to have a wall thickness of 10 mils±2 mils (0.254 millimeters±0.051 millimeters).

Flow conduit assembly 200 can, for example, include sealing end rings 242 and 244 to which the ends of flow conduit 240 are attached. Rearward (relative to the flow of blood through flow conduit 240 from heart 10) end ring 244 can, for example, have attached thereto a curved connective portion 205 for connection to ascending aorta 22 which corresponds generally to the form of ascending aorta 22 as it is connected to heart 10 and assists in positioning the blood flow path of conduit assembly 200 in line with ascending aorta 22. A connector such as suturable connectors 208 (illustrated in FIG. 4B, which can, for example, be formed of a polymeric material such as a urethane polymer) for connecting end ring 244/flow conduit 240 to ascending aorta 22 can, for example, be placed in sealed connection with end ring 244.

A space or volume 212 surrounding flow conduit 240 and bounded and sealed by housing 210 can, for example, be filled with a fluid (that is, a liquid, sometimes referred to herein as the peri-bellows fluid). The fluid can, for example, operate, in part, to equalize pressure within housing 210 and outside of flow conduit 240 with the pressure within flow conduit 240. The fluid in space 212 can, for example, be a blood compatible, aqueous salt solution (including, for example, sodium chloride). In a number of embodiments, the salt solution has an osmotic pressure, an osmolarity or an osmolality approximately equal to that of blood (for example, an osmolarity within 5% or even within 2% of the osmolarity of blood).

As described above, in the case that, for example, a semi-permeable material (such as an elastomeric polymer) is used for fluid conduit 240, the fluid/liquid may, for example, exhibit a similar osmolarity/osmotic pressure to that of blood to, for example, prevent fluid from moving into or out of peri-bellows space 212. Such fluid movement could, for example, damage flexible fluid conduit or bellows 240 either by the fluid conduit 240 rubbing against case or housing 210 upon fluid volume shrinkage or crinkling of fluid conduit 240 upon fluid volume expansion. Fluid movement into or out of the housing of pump system 100 (and thus a change of the volume of fluid within the housing) can occur because of the semi-permeable nature of polyurethane and/or other materials (in which a fluid can be transported through the material) which may be used in flexible fluid conduit 240 where there is a significant osmotic pressure difference across flexible conduit 240. Human blood contains 292 plus or minus ~12 milliosmols of osmotic pressure. A sodium chloride aqueous solution of approximately 0.852% by weight approximately matches blood osmotic pressure and can be used to limit or prevent fluid movement into or out of the space 212. Further, aqueous salt solutions such a sodium chloride aqueous fluid solution in space 212 also provides the advantage of being biocompatible if released into the blood stream.

In the case that fluid conduit 240 is impermeable to the aqueous fluid/liquid surrounding flow conduit 240, it may not be necessary to match the osmolarity of the aqueous fluid to that of blood. In the case that a semipermeable polymeric material such as BIONATE is used for fluid conduit 240, the outer surface thereof can, for example, be surrounded with or coated by a layer of a flexible, impermeable polymer or other impermeable material to reduce or eliminate permeability.

In a number of embodiments, the fluid within space 212 also surrounds the components of rotary-to-linear converter 180 and the components of speed reducer 140 and also fills the space of volume between stator rotor 124 and rotor 126. The fluid can also fill a space 123 between the rotary motor components (for example, bearings 130 and stator 124) and housing 123. Rotary motor 120 can, for example, be spaced from housing 122 and fixed or stabilized in position relative thereto by spacer or standoffs 122' (see FIG. 4C) which can, for example, be formed from an insulating material. Gases can, for example, be eliminated from all volumes within pump system 100, including from within housing 210 and housing 122. As known to those skilled in the medical arts, release of a gas into the bloodstream can have serious adverse consequences. Oily fluid or hydrophobic lubricant, normally used within motors and/or mechanical linkages can also be injurious because oil/hydrophobic lubricant, upon release, can flow downstream in the arterial system and can cause viscous blockage in distant smaller blood vessels. Such blockage can result in cerebral vascular strokes and failure of other vital organs such as the kidneys. Including the fluid or peri-bellows fluid within space 212 of housing 210 and within housing 122 (which can, for example, be in fluid connection with housing 210) to bathe components of motor 120, speed reducer 160 and converter 180, eliminates gases. Moreover, the fluid can operate to dissipate heat from pump system 100. Motion of valve assembly 300 results in circulation or movement of the bathing fluid within pump system 100 and heat can be dissipated, for example, to the blood stream via flow conduit 240.

A lubricant, which can, for example, be a biocompatible, aqueous or hydrophilic lubricant can, for example, be included in the bathing fluid. An example of such a fluid is the glycosaminoglycan hyaluronic acid, which occurs naturally in the body.

As valve assembly 300 moves forward (that is, in the direction of blood flow from left ventricle 14 of heart 10), one or more openings or ports thereof are closed and valve assembly 300 drives blood forward toward the upper portion of ascending aorta 22. The motion of valve assembly 300 is then reversed and it's port(s) are opened, allowing the momentum of the blood to continue forward blood flow.

In the illustrated embodiment, valve assembly 300 includes a single port 320 having a generally circular shape (see, for example, FIG. 3A) and is closed or opened via one or a plurality of movable closure members 330 (two in the illustrated embodiment). Port 320 can, for example, have a diameter approximately equal to the diameter of the ascending aorta. Closure members 330 can, for example, rotate to a closed position (see, FIG. 4B) and to a range of open positions (see, FIGS. 3A and 4C) via shafts or rods 332. In the fully open position, closure members 330 can, for example, be oriented substantially parallel to flow to reduce resistance and to reduce the potential blood strain/shear. Pressure from blood within flow conduit 240 can, for example, be used to open and close closure members 330. If, for example, power to pump system 100 fails or pump system 100 otherwise malfunctions, closure members 330 can still be opened by blood flow from the heart. In that regard, as the closure members 330 can be designed to require only a few millimeters of mercury or less increased pressure to open and pump blood therethrough, blood is free to flow through pump system 100 even if pump system 100 is inoperable.

The distance traveled in any one direction by valve assembly 300 can, for example, be in the range of approximately 1 to 2 centimeters. The cross sectional area of the blood contacting surface of valve assembly 300 can, for example, be approximately 10 square centimeters. As one example, the valve stroke of such a valve assembly can be 1.5 centimeters, resulting in a displaced volume of 15 milliliters. It has been found by experimentation that at cycle rates between, for example, 10 and 16 cycles per second, an aqueous fluid will flow continuously forward because of a momentum effect even though roughly half the time valve assembly 300 is moving backwards. For example, three cycles of 1.5 centimeter valve movement of the above-described valve assembly displaces roughly 3 times 15 or 45 milliliters of blood, and the actual flow in the forward direction could be the same or even greater than this amount. This output provide sufficient extra flow to compensate for the low cardiac output found in typical heart failure. In a number of embodiments, valve thickness and end ring thicknesses are kept below approximately 70 mils (1.78 mm) and approximately 100 mils (2.54 mm), respectively, to facilitate stroke lengths and flow assist volumes as described above.

In the illustrated embodiment, a valve assembly carriage or bearing assembly 400 (see, for example, FIGS. 6A through 6D), which can, for example, include linear rolling element bearings 405, is provided to constrain and align the reciprocating (or forward and backward) motion of valve assembly 300. Valve support structure or valve ring 310 can, for example, be operatively connected to or captured by an annular connector 410 of bearing assembly 400. Annular connector 410 is operatively connected to rotary-to-linear converter 180 so that annular connector 410 (and thereby valve assembly 300) is driven in a reciprocating linear manner by drive system 110.

Figure 6A:
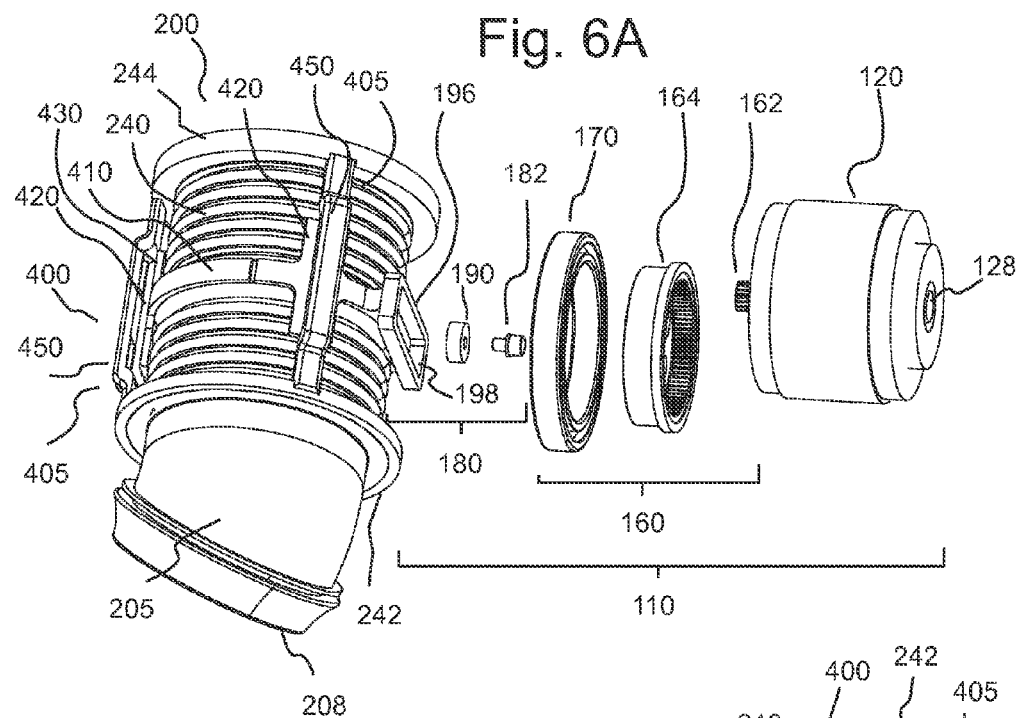
FIG. 6A illustrates a perspective, exploded or disassembled view of the pump system of FIG. 2 with the housing sections removed.

Annular connector 410 can, for example, be operatively connected to a plurality of generally linear rolling element bearings 405 (three in the illustrated embodiment). See, for example, FIGS. 6A through 6E. Each linear rolling element bearing 405 includes an inner race member 420 (which can be connected to or formed integrally or monolithically with annular connector 410) and an outer race member 450. As illustrated in FIG. 6D, each of inner (relative to axis $A_1$) race members 420, can include one or more races 430. In the illustrated embodiment, linear races 430 include a central, gear or toothed section 432. On each side of gear section 432 are bearing surfaces 434 which can, for example, be angled or tapered. In the embodiment illustrated in FIGS. 6D and 6E, a dual taper is provided wherein the bearing surface 434 first tapers inward (with respect to axis $A_1$) as it extends from gear section 432 and then outward. As set forth above, for each race member 420 of linear rolling element bearings 405, a corresponding outer race member 450 (relative to axis $A_1$) is provided. Race members 450 are seated in or fixed to end members or rings 242 and 244 (to which conduit 240 can be attached by, for example, an adhesive). End members 242 and 244 can, for example, be fixed in position relative to each other via race members 450 and/or operative connection with housing 210. Race members 450 include one or more linear races (not shown) which are generally identical to races 430.

Roller elements or rollers 460 are operatively connected between races 430 of inner race members 420 and the races of outer race members 450. Roller elements 460 include a central gear or toothed section 462 and bearing surfaces 464 on each side thereof. Bearing surfaces 464 are angled, tapered or canted in the illustrated embodiment to include a dual taper corresponding to and mating with dual tapered bearing surfaces 434 of races 430 and the dual tapered bearing surfaces (not shown) of the races of outer race members 450.

As annular connector 410 is driven in a linear reciprocating manner to drive valve assembly 300, roller elements 460 roll along races 430 of inner race members 420 and along the races of outer race members 450. The relative positions of roller bearing elements 460 on a race are fixed by the cooperation or intermeshing of central gear section 462 and the gear sections of the bordering races. As described above for rolling element bearing 130, cages are not required between roller elements 460.

In the embodiment illustrated, for example, in FIGS. 6A through 6E rotary motion from ring gear 164 of speed reducer 160 (which can, for example, reduce the rotational speed of rotary motor 120 by 3 to 8 times) is converted to linear motion, for example, using a post or extending member 182 in eccentric connection with ring gear 164. A rotating member 190 (in the form, for example, of a rolling element bearing) is connected to post 182 via a passage 192 therein. Rotating member 190 can, for example, include a radially inward positioned gear wheel 193, a radially outward positioned, rotating ring 194 including a race 194a, and a plurality of rolling elements 195 therebetween. Rotating member 190 engages and follows a cam element or surface 198 of a cam member 196 which is connected to annular connector 410 (and thereby to valve assembly 300) to move valve assembly 300 in a linear reciprocating manner. As described above, linear motion of valve assembly 300 is supported and aligned by linear rolling element bearings 405. Aspects of the linear reciprocating motion of valve assembly 300 can be adjusted by variance of cam element 198. For example, valve assembly 300 can be returned to its rearwardmost position during the backward with a different velocity profile than the velocity profile of the forward stroke.

FIG. 6D illustrates another system or mechanism for translating rotary motion to the linear, reciprocating motion of valve assembly 300. A connecting arm or crank 190', which includes rolling element bearings 195' at each end thereof (as described in connection with rotating member 190), is connected to post 182 at one end thereof and to annular connector 410 at the other end thereof. Connecting arm 190' provides translation of the rotary motion of speed reducer 180 to linear motion. In this type of rotary-to-linear translation or conversion, the amount of rotation of ring gear 164 required for a forward stroke of valve assembly 300 can be different from the amount of rotation of ring gear 164 for a rearward stoke of valve assembly 300. For example, in one embodiment, greater than half of a full ring gear rotation cycle is used for driving the forward stroke of valve assembly 300. By offsetting the position of the bearing of ring gear 164 from the linear direction of valve assembly movement, the ratio of this unequal translation can be varied. Converters for converting the rotary or rotational motion of rotary motor 120 to a nonlinear or curvilinear, reciprocating motion can be provided if it is desired to drive valve assembly 300 in a nonlinear or curvilinear, reciprocating manner.

FIGS. 7A through 7E illustrate an alternative embodiment of a linear rolling element bearing 405' that can, for example, be used in connection with bearing assembly 400. A first race member 420' includes a linear race 430'. In the illustrated embodiment, linear race 430' includes a central, gear or toothed section 432'. On each side of gear section 432' are bearing surfaces 434', which are angled or tapered. A second race member 450' includes a linear race 452' including a central, gear or toothed section 454'. On each side of gear section 454' are bearing surfaces 456', which are angled or tapered. One or more geared rolling elements 460' are positioned between first race member 430 and second race member 450 so that a gear section 462' of roller elements 460' intermeshes with gear sections 432' and 454' of races 430' and 452'. Angled or tapered bearing surfaces 464' extend laterally outwardly from each side of gear section 462' of roller elements 460'. In the illustrated embodiment of FIGS. 7A through 7E, bearing surface 464' angle or taper radially outward (relative to axis $A_3$ thereof—see FIG. 7E) as they extend away from gear section 462'.

The geared roller elements of the rolling element bearings described above each include an intermediate or central gear section from which tapered bearing surfaces extend. However, roller elements including two geared sections having an intermediate roller bearing surface extending therebetween can be used. The intermediate roller bearing surface can, for example, have a generally circular cross section that changes in diameter over the length thereof to provide an angled, tapered or canted bearing surface. As also described above, other types of bearings, and particularly rolling element bearings, including ball bearings with races can be suitable for at least some mechanical linkages of the pump systems hereof.

Pump lifetime reliability considerations described above are complicated when the fluid surrounding flow conduit or bellows 240 also bathes the mechanical motor to valve assembly linkage. Once again, this fluid should be compatible with blood so that if any leakage of this fluid should occur into the blood stream, such peri-bellows fluid would not result in significant or any injury to the patient. As described above, oily or hydrophobic lubricant fluid, normally used with mechanical linkages having multiple bearings would be injurious if released. A truly blood compatible fluid can, for example, include dissolved sodium chloride and possibly other salts in similar concentrations as found in the blood. However, such salt solutions are quite corrosive when placed in contact with virtually all bearing hard steels, including so-called bearing hard 440 series stainless steels. In a number of embodiments hereof, bearing-hard, nitrided martensitic stainless steel (for example, CRONIDUR R 30™, available from Energietechnik Essen GmgH of Essen, Germany) that is corrosion resistant is used in the bearings or rolling element bearings of pump system 100. See German Patent No. DE3901470, the disclosure of which is incorporated herein by reference. Bearings including races and/or rolling elements formed from CRONIDUR are, for example, available from The Barden Corporation. Further, bearings having races and/or rolling elements made from a hard ceramic material can be used to provide corrosion resistance and suitable lifetime requirements.

In addition to the risk of bearing corrosion, there is also a risk of corrosion of copper wire conductors of rotary motor stator 124. Corrosion of such wires when exposed to the corrosive salt water environment of the fluid within housing sections 122 and 210 poses a failure mode for pump system 100. To lessen or eliminate this risk, stator 124 can, for example, be sealed in a hermetically welded titanium case using feedthroughs and sealed crimp joints to connect the copper wires of stator 124 with corrosive resistant conductors such as, for example, platinum wire in the feedthroughs and DFT® silver filled stainless tubing conductors in the leads exiting the motor stator hermetically sealed case. DFT® wire is a metal-to-metal composite available from Fort Wayne Metals of Fort Wayne, Ind.

Using, for example, a three dimensional depiction of the human anatomy surrounding ascending aorta 22, as found, for example, in the commercially available Visual Human software produced by the University of Washington Medical School, one can analyze the dimensions of the various organs in this peri-aortic space. In the case of pump system 100, the volume of drive system 110 (including, rotary motor 120, speed reducer 160 and rotary-to-linear convertor 180) can fit within the volume of lung space without significantly impinging on the other critical structures. As described above, the components of drive system 110 can, for example, be generally cylindrical in shape and extend into the right lung space in a right anterior oblique direction from the aorta at approximately a right angle from flow conduit assembly 200, which can also be generally cylindrical in shape. As described above, the displacement volume of drive system 110 may be made as small as, for example, less than 150 cc, less than 100 cc, or even less than 50 cc. As also described above, distance $D_1$ from axis $A_1$ to the distal end of housing section 122 of drive system 110 may, for example, be less than 12 cm, less than 10 cm or even less than 8 cm. The amount of sacrificed lung volume arising from pump system 100 should not significantly affect lung function, given, for example, an average right lung volume of 3200 cc.

Compared with currently available implantable heart assist pump systems, system 100 affords substantial functional improvements and minimally impacts upon surrounding organs and their function (and, particularly, minimally impacts lung function).

As discussed above, left ventricle 14 is typically weak in heart failure, and the forward strokes of moving valve assembly 300 add an assist or boost to blood coming from the left ventricle 14. Closure members 330 of valve assembly 300 are constructed so that closure members 330 move toward a closed position to close or to substantially close opening or port 320 when the forward velocity of valve assembly 300 is greater than the ambient blood flow velocity. In a number of embodiments, opening 320 is substantially sealingly closed during at least some portion of the forward stroke of valve assembly 300. "Leaking" blood flowing through one or more small openings between closure members 330 and valve support structure 310 during the forward stroke of valve assembly 300 may, for example, activate blood platelets, which can lead to blood clotting and, for example, strokes. When valve assembly 300 is returning or travelling rearward, port 320 opens because the forward blood velocity during left ventricle contraction is always greater than backward moving valve assembly 300 velocity.

Bench testing with high speed photography of valve assembly movement has revealed that a valve assembly such as valve assembly 300 typically requires approximately one third of its forward stroke to cause closure members 330 to move to a closed position to close port 320. Delayed valve closing during a forward valve stroke was found to be responsible for a significant loss in flow boosting efficiency of valve assembly 300. Testing of pump efficiency when closure members were moved/forced to a closed position at or around the beginning of the forward stroke (for example, near the end of the rearward valve stroke and just prior to the forward stroke) of a valve assembly such as valve assembly 300 demonstrated substantial improvement in pumping efficiency.

In this regard, testing demonstrated that actively moving the closure members of a valve assembly toward a closed position to close the valve opening at the beginning of the forward stroke can increase pumping efficiency by approximately 50 percent. Actively moving closure members of a moving valve pump system toward a closed state is thus desirable for the purpose of increasing pump efficiency. As used herein, the term "actively" refers to using one or more devices, mechanisms, systems and/or methods for moving closure members toward an open or closed position or state independent of the force asserted upon the closure members by blood flow. Actively moving the closure members of a valve assembly in a moving valve pump system can, for example, be effected using a mechanism or system that activates closure member movement based on the position of the valve assembly.

Figure 6B:
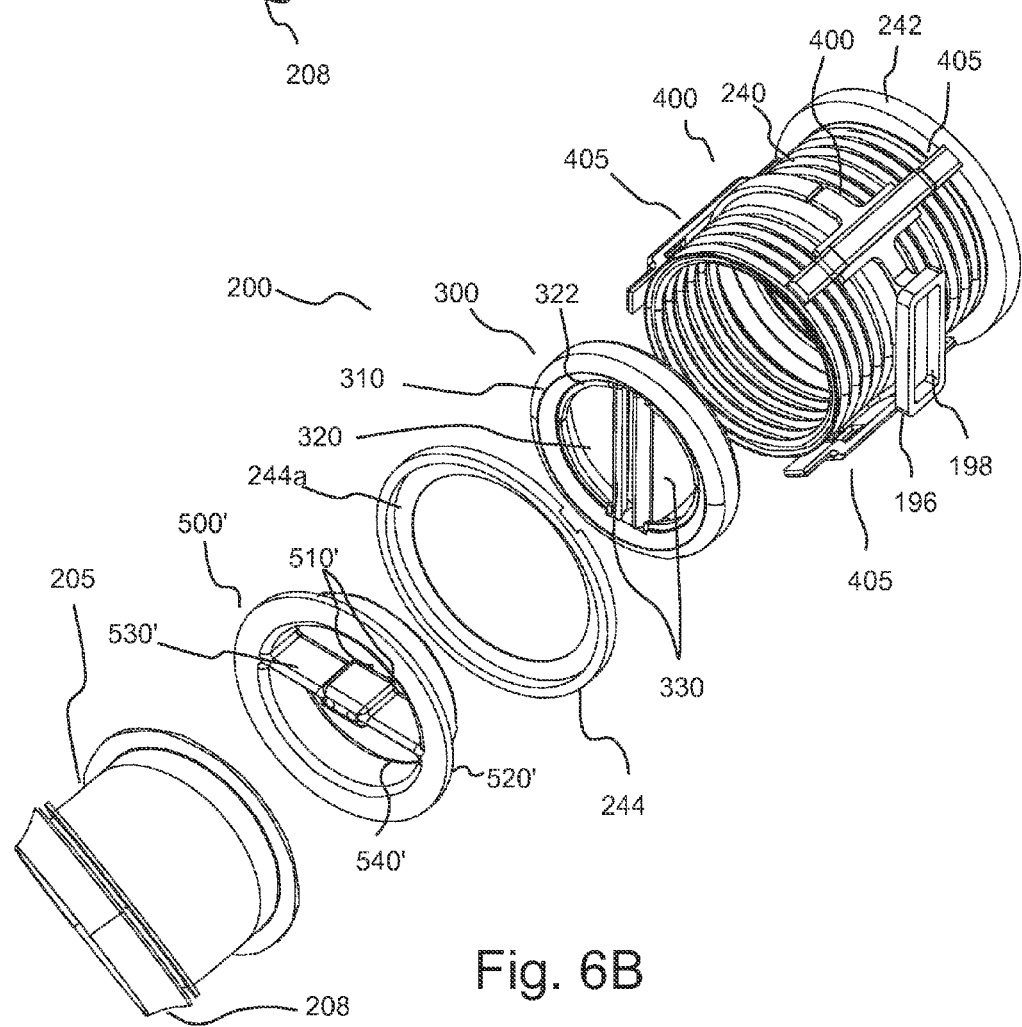
FIG. 6B illustrates a perspective, exploded or disassembled view of a flow conduit assembly and curved connector of the pump system of FIG. 2 with the housing section of the flow conduit removed.

A valve closure member activating device or system can, for example, be a component of valve assembly 300 or be a component separate from, but in operative connection with, valve assembly 300. In a number of embodiments, such an activating system can, for example, include a component positioned within the blood flow pathway of flow conduit 240. Referring to FIGS. 4B, 4C and 6B, an activating system 500' is illustrated which includes one or more abutment members 510'. In the illustrated embodiment, activating system 500' includes an annular support 520' which seats in seating 244a of end member or ring 244 of flow conduit assembly 200 by contact with seating 244a (see FIG. 6B), which in the illustrated embodiment is a radially inward extending flange. Abutment members 510'' are connected to and project forward (relative to the flow of blood from the heart) from a support member 530' that transverses and bisects opening 540' in valve closure system 500' through which blood can flow.

In FIG. 4C, valve assembly 300 is located in its mid-stroke position, traveling backward with closure members 330 in an open position. In FIG. 4B, valve assembly 300 is illustrated at its rearwardmost position. As valve assembly 300 approaches its rearwardmost position, closure members 330 contact abutment members 510 in the vicinity of the radially inward edge of closure members 330, causing closure members 330 to rotate toward the closed position illustrated in FIG. 4B, in which the radially outer edges or periphery of closure members 330 contact a radially inward projecting seating or flange 322 on valve support structure or valve ring 310. Relatively tight coaptation of the closure members 310 on flange 322 can be effected to limit or prevent blood leakage when valve assembly 300 is closed (that is, when closure members 310 are in the closed position).

In the case of activating system 500, support member 530 and abutment members 510 are located in the blood stream to contact closure members 330 and force closure members 330 toward the closed position as the valve assembly 300 is moved to its rearwardmost position. In certain situations, the presence of such components in the blood stream can increase the risk of clotting. Such a risk can be substantially reduced or eliminated by positioning a valve closure system outside of or separate from the blood flow path.

In several embodiments of closure member activating systems hereof, the activating system is outside of or sealed from the blood flow path through the pump system (that is, outside or sealed from the flow path of flow conduit 240 in the case of pump system 10). In a number of such embodiments, at least one component of the valve closure members (or a component attached thereto) which moves (for example, rotates or pivots) with the valve closure members extends through at least a portion of the valve support structure so that the movement thereof (and, thereby, the movement of the valve closure members from and/or toward the closed to open positions) can be controlled by the activating system which resides outside of the flow path of blood through the pump system.

A seal can, for example, be provided around a component in operative connection with the closure members which extends through the valve support structure to prevent blood from exiting the pump system flow path. In the case of a pump system to be implanted for an extended period of time as discussed above, such a seal should be designed to survive more than a billion valve assembly stroke cycles over the life of the pump system. Typically, seals on moving components (for example, rotating shafts, rods or axels) include tight fitting bushings which compress against the moving component to create the seal. In the case of a blood contacting seal for a moving component and, particularly, for a component that will be moved through a very high number of cycles, bushings or compression seals present a number of problems. For example, there is a small crevice at the interface between the seal and the moving component (for example, at an axel-bushing joint) at which (at the microscopic blood cell level) some degree of undesirable blood cell shear and/or crushing can occur. Further, compression seals such as bushing are subject to wear over time. To compensate for problems associated with wear, elastic compression of the seal against the moving component is typically employed. However, such compression changes with wear, and a certain amount of force/torque exerted by the seal must be overcome to move the moving component. With wear over time, the resisting force/torque exerted by the compression seal can change, which complicates the design of a reliable valve closure system.

In several embodiments, seals hereof include a first connecting member attachable to a moving component so that it moves with the moving component, but not relative thereto, and a flexible sealing member attached to the first connecting member. The flexible sealing member is fixed to, for example, the valve support. Such a seal can, for example, include a first connecting member attached to a moving component so that it moves with the moving component, but not relative thereto, a second connecting member attached to a another component (which can be movable or stationary) and a flexible sealing member extending between the first connecting member and the second connecting member. The flexible sealing members can, for example, be formed as a layer, film, sheet or membrane through which the fluid to be sealed has limited or no mobility.

Figure 8A:
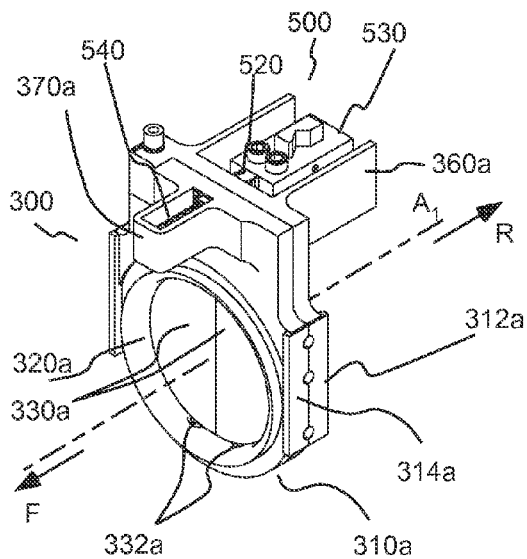
FIG. 8A illustrates a perspective view another embodiment of a valve assembly hereof including a closure member activating system to actively move the closure members toward and open position or toward a closed position.

In a number of embodiments, closure members similar to closure members 330 are used in pump systems hereof wherein the axels, shafts or rods fixed to the closure members are extended to pass through at least a portion of the valve support structure and to extend outside of the flow conduit. FIGS. 8A through 8N illustrate another embodiment of a valve assembly 300a including a valve support structure 310a (see FIG. 8A), closure members 330a and shafts 332a. Shafts 332a extend through at least a portion of support structure 310a so that a portion of shaft 332a is outside of and/or sealed from the blood flow path through flow conduit 240 of pump system 10 (or another moving valve pump system hereof). A seal 340a, which can be positioned within a seating formed in support structure 310a, is fixed to shaft 332a, which passes through an opening or passage 342a of seal 340a. Seal 340a can, for example, be fixed to shaft 332a via a first connecting member 344a (see FIGS. 8D and 8E). Connecting member 342a and that portion of a flexible sealing members 348 compressed against shaft 332a by first connecting member 342a move with shaft 332a but not relative to the shaft 332a. Seal 340a is also fixed to support structure 310a. Seal 340a can, for example, be fixed to support structure 310a via a second connecting member 346a thereof. During rotation of shaft 332a relative to support structure 310a, the portion or section of flexible sealing member 348a extending between the first connecting member 344a and the second connecting member 346a is torsionally strained to accommodate the rotation of shaft 332a. In the illustrated embodiment, flexible sealing member 340a can, for example, be an annular member wherein a longitudinal cross-section or cutaway view appears as two U-shaped sections (see FIG. 8E). This form can also be described as a generally U-shaped element revolved about an axis. Flexible sealing member 340a can, for example, be formed from a fatigue resistant, flexible material (for example, an elastomeric polyurethane such as BIONATE).

Each of first connecting member 344a and second connecting member 346a can, for example, include a biasing or spring-loaded annular member (for example, a metallic ring). Inner, first connecting member 344a biases to seal the inner arm or section 347a of the U-shaped annulus of flexible sealing member 348 against shaft 332a (see radially inward directed arrows in FIG. 8F). Outer, second connecting member 346a biases to seal the outer arm or section 349a of the U-shaped annulus of flexible sealing member 348a against the surface or wall of the corresponding seating within valve support structure 310a (see radially outward directed arrows in FIG. 8E). The annular space between shaft 332a and the wall valve support structure 310a is thereby sealed without creating a crevice between elements which are in relative motion. Sixty to 90 degrees or more of shaft rotation can, for example occur without breaking the seal by placing sealing member 348a under torsional strain during rotation of shaft 332a. The torsional strain can be lessened by providing (for example, in a polymer processing procedure such as a molding procedure) slack in flexible sealing member 348a and by mounting seal 340a (that is, fixing seal 340a to shaft 332a and to support structure 310a wherein flexible sealing member 348a is in a substantially or totally unstrained state) when shaft 332a and closure member 332a are positioned midway in the expected range of rotation thereof. For example, if closure members 330a can rotate between 0 and 90 degrees, seals 340a can be mounted to shafts 332a when closure members 330a are positioned at approximately 45 degrees.

Each of first connecting member 344a and second connecting member 346a can, for example, be formed as a split ring. An assembler can, for example, compress the ring of second connecting member 346a with dedicated pliers and insert the ring into the sealing annulus of flexible sealing member 348a. The assembler can then release the ring to expand the ring and force outer wall 349a of flexible sealing member 348a radially outwardly against the wall of valve support structure 310a to achieve a fluid seal therewith. Similarly, dedicated pliers can, for example, be used to expand the ring of inner, first connecting member 344a to a more open position and, when in proper position around shaft 332a and around inner member 347a of flexible sealing member 348a, release the ring to contract, thereby compressing inner wall 347a of flexible sealing member 348a against shaft 332a to achieve a fluid seal therewith.

Other components of valve assembly 300a can, for example, present difficulties with or interfere with the installation of seals 340a (for example, in forming a sealing connection with valve support structure 310a). To facilitate installation of seals 340a, seals 340a can first be installed to form a sealed connection with an outer sleeve or sheath 370 and with shaft 332a as illustrated in FIGS. 8G and 8H. Sleeve or sheath 370a can, for example, be a length of hollow, cylindrical metal tubing. Outer wall 349a of flexible sealing member 348a is sealed to an inner wall of sleeve or sheath 370a as described above. Assembly of sections 312a and 314a of valve support structure 310a can cause compression of sleeve or sheath 370 therebetween to form a sealed engagement with valve support structure 310a.

To assist in providing proper alignment and relatively free movement thereof, each shaft 332a can cooperate with (for example, pass through) one or more bearings. In the embodiment of FIGS. 8A through 8N, each shaft 332a is mounted within two rolling element bearings 350a as described above to properly align each shaft 332a and minimize torque required to rotate closure members. As described above, geared roller elements (not shown in FIGS. 8A through 8N) can be used in rolling element bearing 350a. Moreover, as also described above, because rolling element bearings 350a may be exposed to a corrosive environment, they can, for example, be formed from a corrosion resistant material such as nitrided martensitic stainless steel or a ceramic material. Each shaft 332a of a closure member 330a (two in the embodiment illustrated in FIGS. 8A through 8N) can include two rolling element bearings 350a positioned on shafts 332a at opposite ends of closure members 330a. Roller bearing elements 350a can, for example, be constructed and operate in the manner of roller bearing elements 130 or as otherwise described above. In the illustrated embodiment, each rolling element bearing 350a is sealed from the blood flow path by seals 340a.

External to (or radially outward from, with reference to axis $A_1$) rolling element bearings 350a, at least one end of shafts 332a includes an extending section 332a' (which can be a part of shaft 332a or connected thereto). Rotational activation of extending sections 332a' results in rotation of closure members 330a operatively connected thereto in an opening or closing direction via an activating system such as activating system 500 illustrated, for example, in FIGS. 8A through 8C.

Figure 8B:
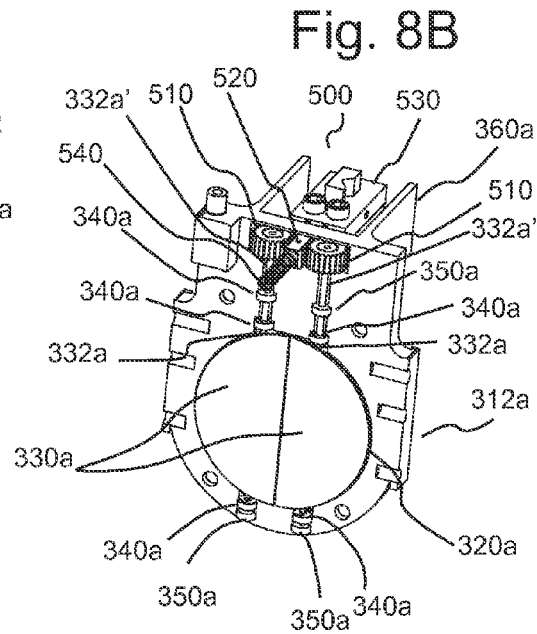
FIG. 8B illustrates a perspective view of a section of the valve assembly of FIG. 8A.
Figure 8C:
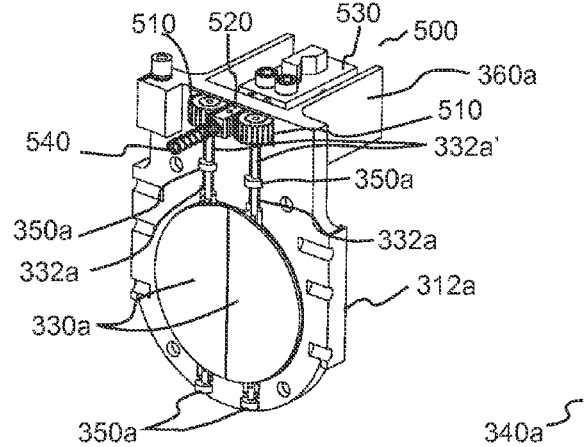
FIG. 8C illustrates another perspective view of a section of the valve assembly of FIG. 8A wherein seals have been removed.
Figure 8D:
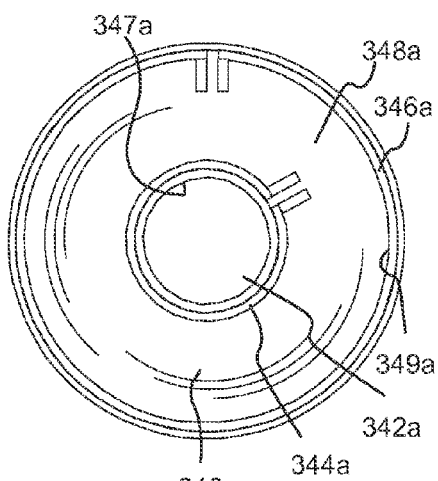
FIG. 8D illustrates a top plan view an embodiment of a seal for use in connection with a shaft of a closure member of the valve assembly of FIG. 8A.
Figure 8E:
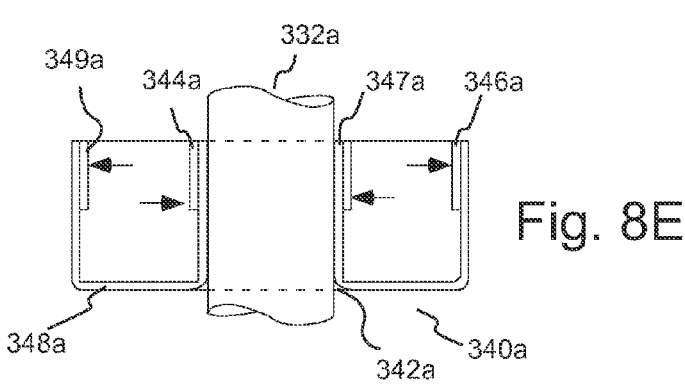
FIG. 8E illustrates a side cutaway view of the seal of FIG. 8D.
Figure 8J:
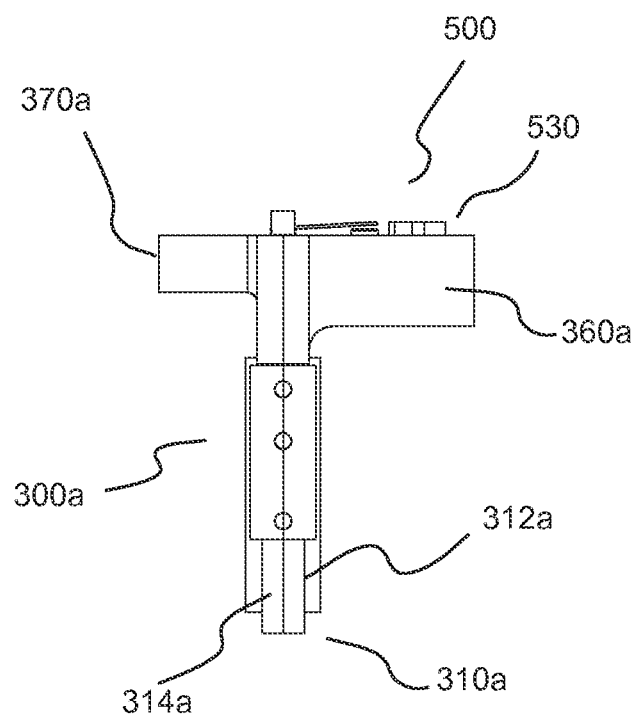
FIG. 8J illustrates a side view of the valve assembly of FIG. 8A with the closure member thereof in a closed position.
Figure 8I:
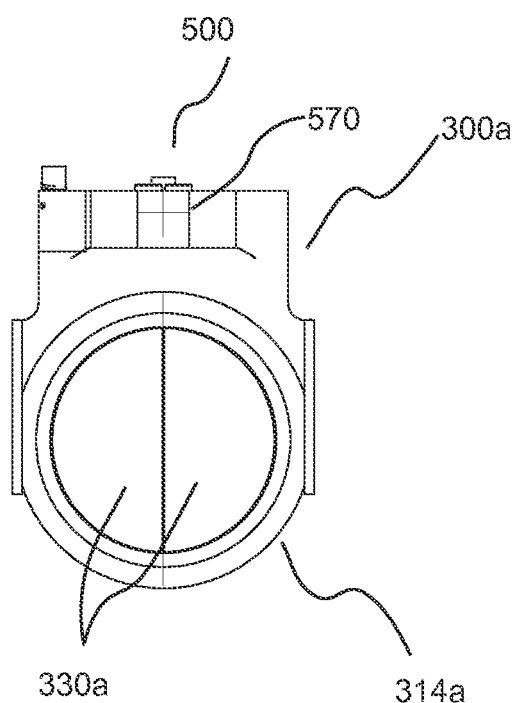
FIG. 8I illustrates a front view of the valve assembly of FIG. 8A with the closure member thereof in a closed position.
Figure 10A:
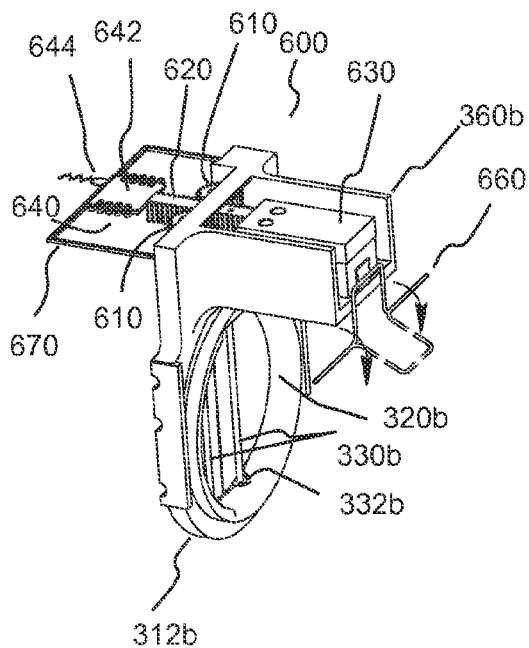
FIG. 10A illustrates a perspective view of a section of another embodiment of a valve assembly hereof including a closure member activating system to actively move the closure members toward and open or toward a closed position.
Figure 10B:
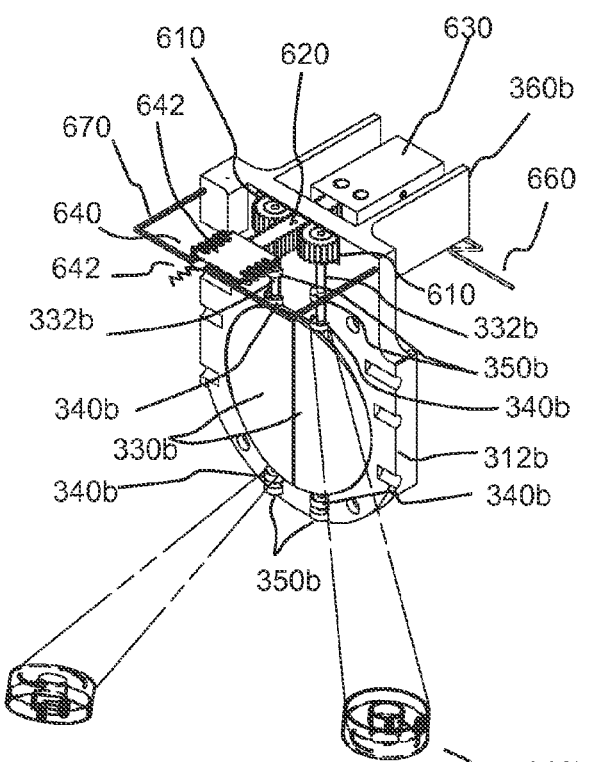
FIG. 10B illustrates another perspective view of the section of the valve assembly of FIG. 10A.
Figure 10C:
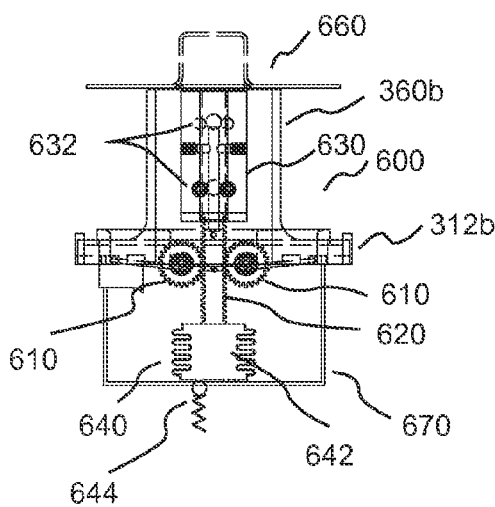
FIG. 10C illustrates a top view of the section of the valve assembly of FIG. 10A wherein an upper closure of a linear rolling element bearing in operative connection with the rack of the activating system is removed.
Figure 10D:
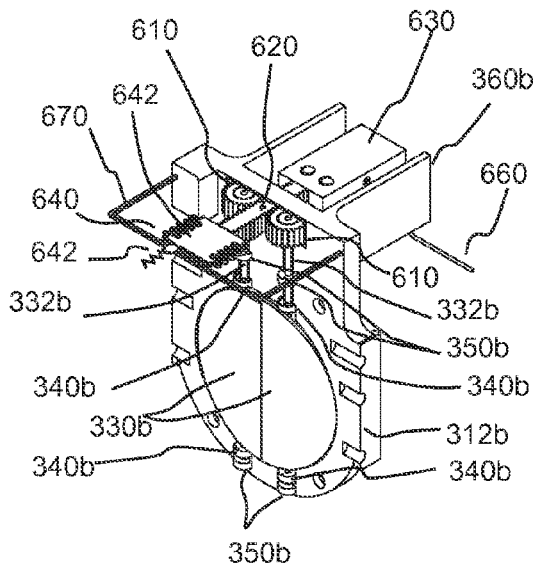
FIG. 10D illustrates compression of a biasing system of the section of the valve assembly of FIG. 10A.
Figure 10E:
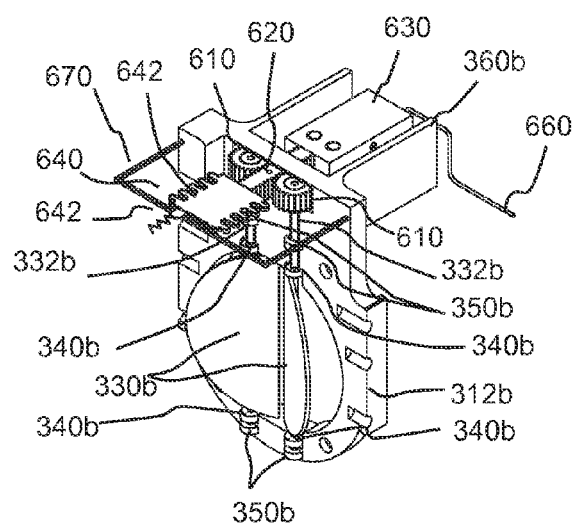
FIG. 10E illustrates the biasing system of FIG. 10E expanding and causing the activating system move the closure members to an open position.
Figure 10F:
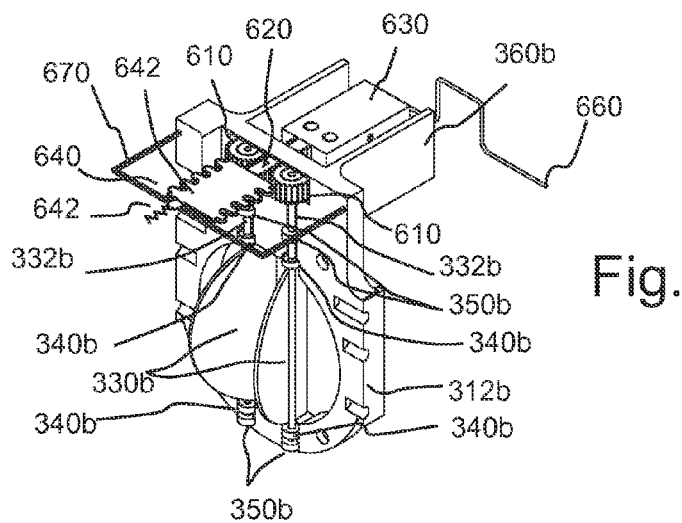
FIG. 10F illustrates the biasing system of FIG. 10E fully expanded so that the activating system has moved the closure members to the fully open position.
Figure 10G:
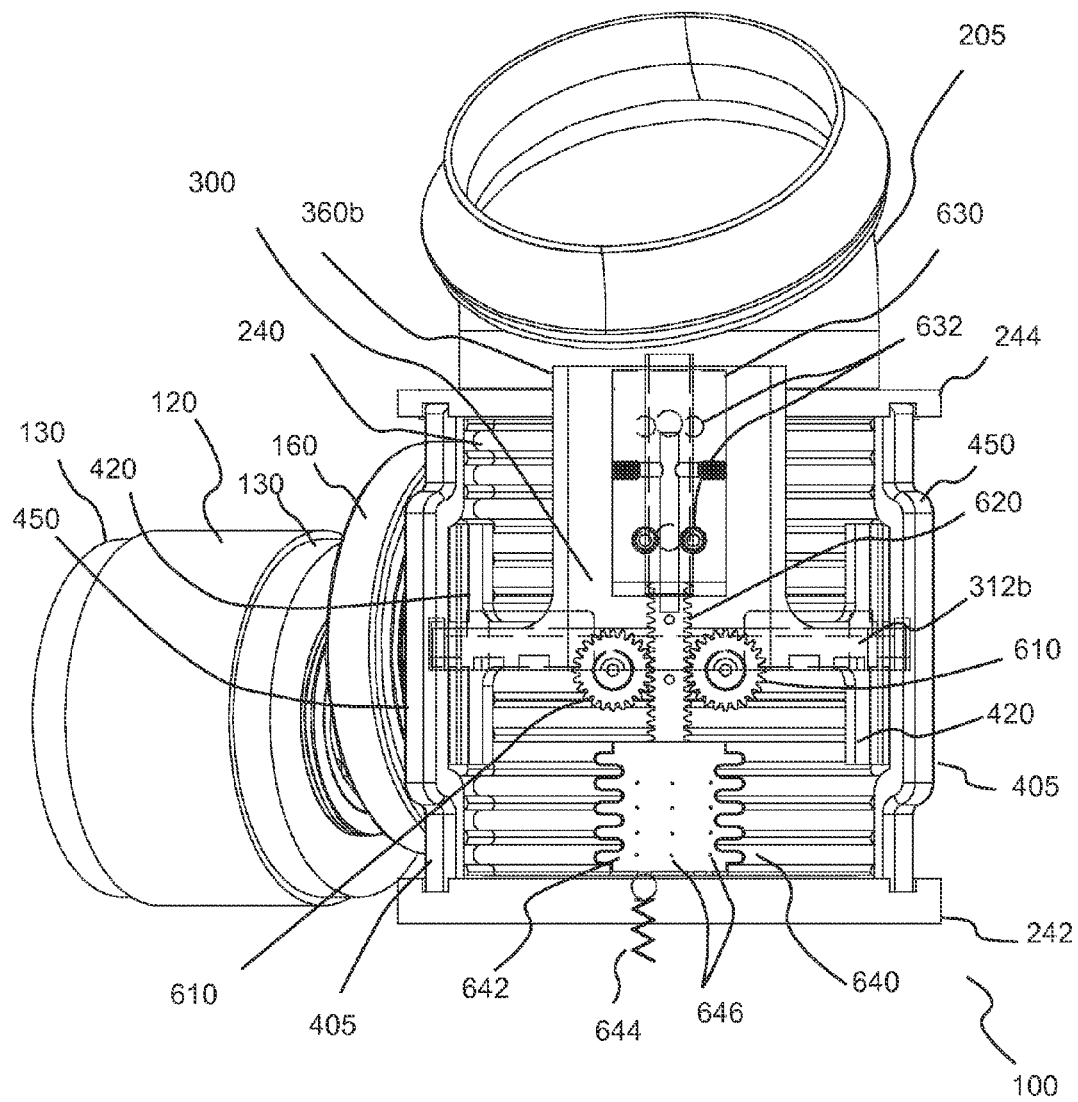
FIG. 10G illustrates pump system 100 with the housing sections thereof removed and the activating system of the valve assembly of FIG. 10A in operative connection therewith (wherein the activating system is enlarged relative to the pump system).

In the illustrated embodiment, valve support structure 310a is formed in two sections 312a and 314a (see FIGS. 8A, 8B and 8C) which are separable from each other along a plane generally perpendicular to axis $A_1$ of pump system 10. Such a construction can facilitate assembly valve assembly 300a, including the mounting of closure member shafts 332a while, for example, in operative connection with associated seals 340a and associated roller element bearings 350a in valve support structure 310a. FIG. 8B illustrates mounting of those components in section 312a of valve support structure 310a. In FIG. 8C, section 312a is illustrated without seals 340a in operative connection with shafts 332a to illustrate the seatings therefor formed in section 314a. Similar seatings (not shown) are formed in section 314a.

In the embodiment illustrated in FIGS. 8A through 8N, closure member activating system 500 is formed at least partially integrally with valve support structure 310a of valve assembly 300. However, the activating system can be formed separately from and in operative connection with valve assembly 300. For example, activating system 500 can be operatively connected to annular connector 410 within housing 210. Activating system 500 includes a positioning mechanism such as a positioning gear 510 in operative connection with (for example, keyed thereto) extending sections 332a' of shafts 332a. A rack 520 including teeth on two sides thereof, which are adapted to mesh with positioning gears 520, is operatively connected between positioning gears 510a. A change in the position of rack 520 along a line generally parallel to axis $A_1$ drives positioning gears 510a and, thereby, shafts 332a and closure members 330a. In that regard, rotational motion of positioning gears 410 imparts rotational motion to extending sections 332a'.

An abutment member (not shown in FIGS. 8A through 8N, but, for example, positioned at a fixed position relative to (and within) housing 210 of flow conduit assembly 200 (with reference to pump system 10) can, for example, contact rack 520 as valve assembly 300a moves rearward (represented by arrow R in FIG. 8A) in the vicinity of the rearwardmost position of valve assembly 300 to drive rack 520 in a forward direction. Forward motion of rack 510 rotates positioning gear 510 on the right side (from the perspective of the viewer of FIGS. 8A through 8C) of rack 520 in a counterclockwise direction and rotates positioning gear 510 on the left side of rack 520 in a clockwise direction to move closure members 330a toward a closed position as illustrated in FIGS. 8A through 8C, 8G and 8H. As, for example, illustrated in FIGS. 8K and 8L, rack 510 can be movable through a linear bearing 530 which limits movement of rack 520 to movement in a single linear direction. Each side of linear bearing 530 can, for example, operate in the manner described above for linear rolling element bearing 405'. Each side of linear rolling element bearing 530 can, for example, include two geared roller elements 532 similar to geared roller elements 460' of rolling element bearing 405'. In the illustrated embodiment, linear rolling element bearing 530 is positioned within a seating 360a which is attached to or formed integrally or monolithically with section 312a.

Rack 520 need, for example, travel only a short distance between the positioning gears 510 to activate closing or opening of both closure members 330a. In one embodiment, positioning gears 510 rotate closure members approximately 90 degrees from a fully open position illustrated in FIGS. 8K through 8N, wherein closure members 330a are oriented generally parallel to the direction of bulk flow of blood through valve opening 320a to a fully closed position as illustrated in FIGS. 8A through 8C, 8I and 8J wherein closure members 330a are oriented generally perpendicular to the direction of bulk flow of blood through opening 320a.

As described above in connection with valve assembly 300, pressure from the flow of blood through valve opening 320a (particularly during rearward movement of or the backstroke of valve assembly 300a) tends to force closure members 330a to an open position. However, a mechanism or system can be provided to, for example, cooperate with activating system 500 to bias closure members 330a to an open position or state (that is, to actively cause movement of closure members 330a toward an open position or state, which is a default or normal state). Activating system 500 can, for example, include or have in operative connection therewith a biasing mechanism or system 540a that applies force to rack 510 to cause rack 510 to move (in the direction of arrow R in FIG. 8A) to open closure members 330a. Biasing mechanism 540a can, for example, bias rack 510 to move sufficiently to rotate closure members 330a (via positioning gears 510) to the fully open state illustrated in FIGS. 8K through 8N when valve assembly 330a is in its backstroke or when, for any reason, pump system 10 or another moving valve pump system incorporating valve assembly 300a is not active (for example, because of power failure or failure of one or more components of the pump system). In the embodiment illustrated in FIGS. 8A through 8N, biasing mechanism 540 includes a spring positioned within a seating 370a attached to or formed integrally or monolithically with section 314a. Biasing mechanism or system 540 assists in preventing extended blockage of the blood flow path in any circumstance.

Shafts 332a can, for example, be formed from a blood compatible polymeric material or a metal such as titanium. Support structure 310a can also be formed from a blood compatible polymeric material or a metal such as titanium. As illustrated in FIGS. 9A through 9E, closure members can include a rigid base member 334a that is, for example, formed by folding a monolithic sheet of metal (for example, a relatively thin, die-cut titanium sheet) around shaft 332a (see FIG. 9E). As used herein in connection with closure members 330a, the term "rigid" refers to a material that does not flex or displace substantially under the forces experience during normal use of pump system 10. A rigid material or structure may deflect less than 0.010 inches per inch under working forces (or forces normally experienced during use of pump system 10), or may deflect less than 0.001 inches per inch under working forces. Such rigid materials may, for example, have a Young's modulus of greater than 5 ksi or greater than 10 ksi. Welds (such as spot welds) can, for example, be used to connect base member 334a to shaft 332a and to connect the folded and overlapped sections of base member 334a to themselves. A blood compatible polymer layer 336a (for example, a polyurethane layer) can then be placed over base member 334a. The material of layer 336a can, for example, be more flexible than the material for rigid base 334a. Such flexible materials, may have a Young's modulus less than 5 ksi or less than 1.5 ksi. For example, a monolithic polyurethane sheet can be laid/folded over base member 334a. The two polyurethane layers of the sheet can, for example, be bonded adhesively or otherwise to base member 334a. In areas (for example, outward of a radial perimeter, edge or periphery of rigid base member 334a. in the vicinity of holes 335a formed in base member 334a, and/or inward of an inner edge of base member 334a) where the two layers of polyurethane directly oppose each other, solvent or heat bonding can, for example, be used to bond the two layers of polyurethane together. Alternatively, a polymer such as a polyurethane (for example, BIONATE) can be injection molded over base or substrate member 334a. As described above in connection with valve assembly 300, the radially outer edge area of closure members 340a, wherein layers 336a (for example, of a flexible material) extend beyond base members 334a, can contact a landing area of the valve support structure upon closing to assist in forming a sealed coaptation. Extending layers 336 beyond an outer edge area of base members 334a can also decrease the likelihood of "bouncing" of closure member 330a when forced to a closed position. Further, extending layers 336a beyond the inner edge of base members 334a can assist in closing or sealing the seam formed between closure members 330a upon closure thereof. In that regard, closure members 330a extend inward beyond shafts 332a to close or seal the area between shafts 332a.

Forming a sealed coaptation with the valve support structure and preventing of bouncing upon closing can also be facilitated with closure members which are rigid around the outer periphery thereof by providing a flexible element on a landing of the valve support structure which is contact by the closure members upon closing.

A situation that may arise during actively moving closure members 330a toward a closed position as valve assembly 300a reaches its rearwardmost position is that the natural flow rate of blood coming from the heart may be greater than the early forward velocity of valve assembly 300a during its forward stroke. In that case, closure members 330a may be opened by biasing mechanism 540a and/or the flowing blood prior to valve assembly 300a reaching a velocity that is greater than the ambient blood flow produced by the heart (at which velocity force exerted upon closure members 330a by the blood forces closure members 330a to a closed state), thereby reducing the pumping efficiency of valve assembly 300a.

A method for limiting or preventing reopening of valve assembly closure members during the early forward stroke of the valve assembly is to include a temporary latching or delaying system that will hold or otherwise maintain the closure members in the closed state for a period of time even if the natural flow from the heart exceeds the velocity of the valve assembly. Such a latching or delaying mechanism can, for example, operate only temporary (for example, until valve velocity exceeds blood flow velocity) to prevent the closure members from being locked in a close position. If the forward stroke of the valve assembly takes, for example, between 30 to 50 milliseconds, the latching or delaying mechanism can, for example, hold or maintain the doors in a close state for approximately 25% of the forward stroke time or roughly 7 to 12 milliseconds. Such a temporary delaying or latching time period may, for example, be accomplished using a biasing system (which biases closure members 332a to an open state) with a timed release mechanism or dampening mechanism that takes, for example, 7 to 12 milliseconds to release the rack and allow the biasing action thereof to compete with the closing force of the valve assembly moving forward at a velocity greater than the natural velocity of the blood stream behind the valve assembly.

FIGS. 10A through 10G illustrate another embodiment of a valve assembly 300b which, in many respects, operates similar to valve assembly 300a. Like components of valve assembly 300b are referenced similarly to corresponding components of valve assembly 300a with the substitution of the designation "b" for the designation "a" following the numeric portion of the reference. Valve assembly 300b includes or has in operative connection therewith a closure member activating system 600 which includes or has in operative connection therewith a biasing system 640. Biasing system 640 includes a latching or delaying system or is dampened to effect the latching or delaying described above. Biasing system 640 can, for example, use fluid movement requiring a period of time (for example, 7 to 12 milliseconds) to release a rack 620 thereof and allow the biasing action of biasing system 640 to compete with the closing force of valve assembly 300b moving forward at a velocity greater than the natural velocity of the blood stream behind valve assembly 300b. Like closure member activating system 500, closure member activating system 600 includes positioning gears 610 connected to extending sections 332b' of shafts 332b. The rotational position of positioning gears 610 is changed by movement of rack 620 which is constrained to linear movement by a linear bearing such as a linear rolling element bearing 630 (including, for example, geared roller elements 632—see FIG. 10C).

Rather than spring biasing mechanism or system 540 of activating system 500, activating system 600 includes biasing system 640, which includes one or more resilient, expandable/compressible enclosures 642 which is/are fluid filled and surrounded by (or immersed in) fluid (for example, filled with and surrounded by the fluid present within housing 210 of fluid conduit assembly 200 and within housing 122 of pump system 10). Filling of enclosure(s) 642 during expansion is controlled in a manner to effect latching or delaying of movement of closure members 330b toward and open state. In the illustrated embodiment, the material of enclosure 642 is folded or corrugated in, for example, the manner of a bellows. Enclosure 642 can, for example, be formed of a resilient metal. Resilient, enclosure or biasing bellows 642 is compressed by forward (with reference to blood flow as discussed in connection with FIG. 8A above) motion of rack 610 upon contact with an abutment member 660 as valve assembly 300b moves rearward (with reference to blood flow) to its rearwardmost position during its backstroke. The resilient nature of enclosure 642 provides a biasing force tending to force rack 610 rearward toward its rearwardmost position, thereby causing closure member 330a to be rotated to an open position. Enclosure 642 can, for example, include one or more one-way check valves 644 (for example, including a spring-loaded, one-way ball valve) in connection with an outlet port thereof that allows fluid to exit but not to enter enclosure 642. To provide for entry of fluid into enclosure 642 at a controlled rate, enclosure 642 includes an inlet system including one or more inlet holes or passages 646 (see FIG. 10F), which can be dimensioned to a predetermined diameter or diameters. In the illustrated embodiment, a plurality of holes 646 having relatively small diameters control flow of fluid into enclosure 642.

When the valve assembly 300 is moved near its rearwardmost position, abutment member 660 engages the free end of rack 610 (opposite the end in operative connection with enclosure 642). Rack 610 is moved forward upon such contact, and enclosure 642 is compressed against a contact member 670. Contact member 670 is connected to activating system 500. Compression of enclosure 642 rapidly forces fluid out of enclosure 642 via one-way valve 644. As describe above, the forward motion of rack 610 rotates positioning gears 610 so that shafts 332b and attached closure members 330b rotate, for example, 90 degrees to a closed position. Inlet hole(s) or passage(s) 646 are dimensioned such that a predetermined range of time (for example, approximately 7 to 12 milliseconds) is required before resilient enclosure 642 begins to refill with fluid flowing through inlet holes 646. As valve assembly 300b accelerates forward, pushing blood, a positive pressure differential develops across closure members 330b that keeps them closed for the remainder of the forward stroke. At the end of the forward stroke, compressed resilient enclosure 642 fills with fluid and expands, forcing rack 610 rearward and opening closure members 330b. When valve assembly 330b moves forward to pump blood, closure members 330b are thus biased or maintained toward a closed or nearly closed position until the velocity of the moving valve assembly 300b exceeds the velocity of the blood exiting the heart. Because collapsed enclosure 642 is filled with a fluid at a controlled refill rate, closure members 330b are held near or at the fully closed position for a controlled time, (for example, 5 to 20 milliseconds or 7 to 12 milliseconds). As described above, when the velocity of moving valve assembly 300b exceeds the velocity of blood coming from the heart, the valve is biased or forced closed by the force of the blood. When valve assembly 300b nears the end of its forward or pumping stroke, it begins to slow down and then reverses. The force of blood upon closure members 330b during this slowing down and reversal drops. Enclosure 642 can then expand and move closure members 330b toward an open position. The force exerted upon closure members 330b upon expansion of enclosure 642 is assisted by the forward flow of blood against the rearward moving closure members 330b.

As a safety or failsafe feature, abutment member or mechanical stop 660, which is fixed to mechanical ground of the pump system 10 (or another moving valve pump system hereof) can be moved "out of the way" by, for example, changing an applied current (that is, either increasing current or decreasing current applied). For example, abutment member 660 can include or be connected to a component such as a shape memory alloy component (for example, a Nitinol component, which is a metal alloy of nickel and titanium), whereby the position of abutment member 660 can be changed by electrically activating/deactivating the shape memory alloy (or other) component of abutment member 660 (which can be the entirety of abutment member 660). In one embodiment, current must be applied to a shape memory alloy component to position abutment member 660 to contact rack 610. If current is removed from the shape memory alloy component, abutment member 660 is moved to a position wherein it cannot contact rack 610 (see, for example, dashed lines in FIGS. 10A through 10C). If the mechanical linkage for moving valve assembly 300b should fail, the pump system should otherwise fail, and/or valve assembly 300b should become stuck when closure members 330b are in the closed position, electric current can be removed from the shape memory alloy component to change its shape and, thereby, change the position of abutment member 660 to release rack 610 to allow resilient enclosure 642 to expand and open closure members 630b. A valve assembly "stuck closed" failure condition can, for example, be sensed by the pump system control electronics 50 (see FIG. 2) when, for example, inappropriate or absent motor movement is combined with abnormally high pressure occurring behind valve assembly 300b with ventricular contraction.

In the case of the moving valve heart assist pumping systems disclosed herein and in other moving valve heart assist pumping systems, timing of valve movement relative to the muscular contraction of left ventricle 14, the main pumping chamber of heart 10 can be important. As described above, typical heart failure patients benefiting from a moving valve heart assist pump system will have a weak left ventricle 14, capable (without assist) of ejecting only a volume of 20 to 40 ml per stroke volume into ascending aorta 22. Such stroke volumes are substantially lower than normal, and as compensation, the heart rate or HR is modestly higher than normal, to help make up some of the blood flow shortfall.

In a number of embodiments of systems, devices and methods hereof, pump system 100 or another moving valve pump system is adapted to be controlled differently for systolic and preserved ejection fraction forms of heart failure are different. In the case of low ejection fraction, systolic failure, there is sufficient blood in the heart from which a moving valve can draw and push into aorta 20, to increase the stroke volume to a normal level or a nearly normal level.

In the case of preserved ejection fraction failure, however, a different treatment strategy may be desirable. A number of systems hereof include a pacemaker to increase the patient's heart rate in combination with a moving valve pump system to lower the strain on the heart's muscle and make it easier for stiff left ventricle 14 to expel blood. As used herein, the term "pacemaker" refers to a device to regulate the beating of the heart, which uses electrical impulses delivered to heart muscles via electrodes contacting the heart muscles. The pacemaker can, for example, increase heart rate at least 20% above normal or natural heart rate. In a number of embodiments, the pacemaker increases heart rate in the range of 20 to 50% above the normal heart rate for a patient.

Figure 11A:
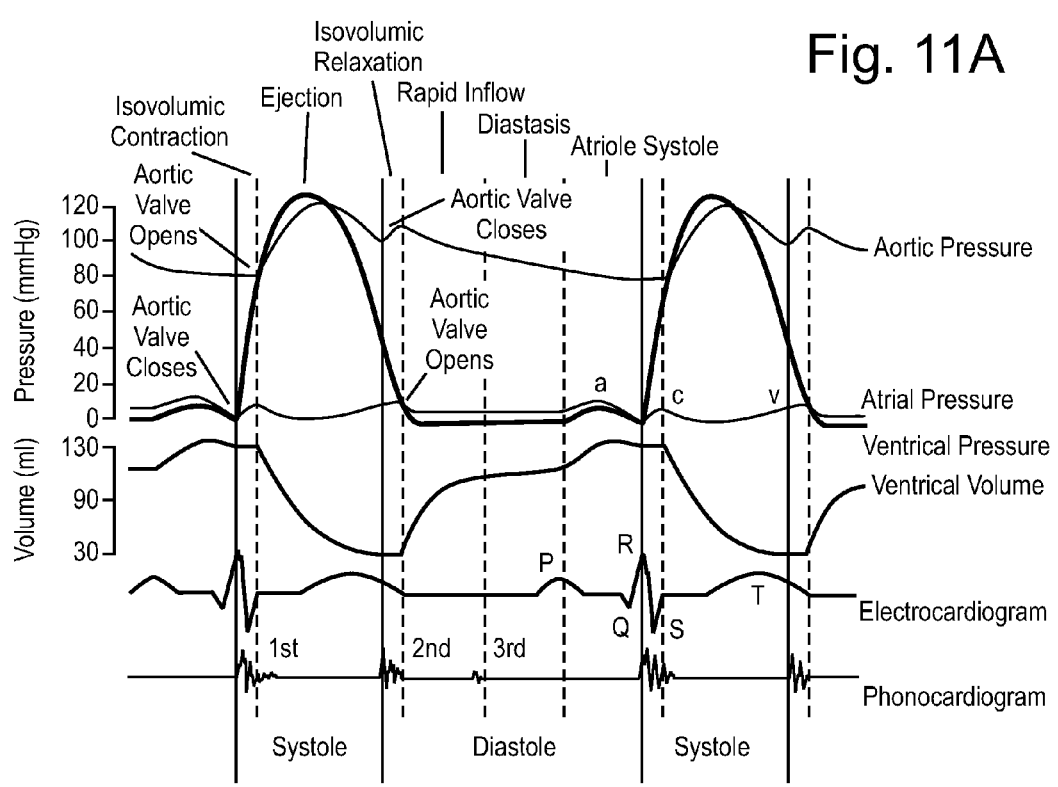
FIG. 11A illustrates the relationship between mechanical activity and electrical activity in the heart.
Figure 11B:
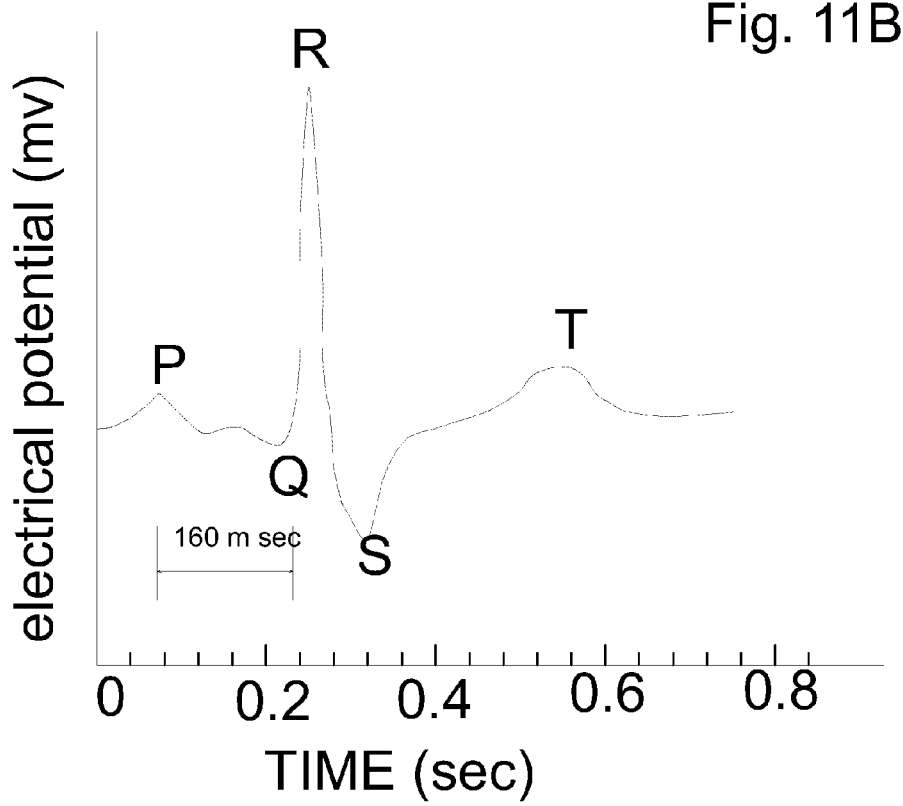
FIG. 11B illustrates a normal EKG with the P wave preceding the start of the QRS complex by approximately 160 milliseconds (ms).

In either form of heart failure, however, the timing of the moving valve's forward stroke(s) in relation to ventricular contraction is important. If the velocity of ejected blood from left ventricle 14 exceeds the velocity of the moving valve, no moving valve assist will occur. In that regard, the velocity of the moving valve must be greater than that of the ambient blood flow for the moving valve to have purchase on the blood and push it forward. Thus, with either systolic failure of preserved ejection fraction failure, it can be desirable to operate the moving valve when left ventricle 14 is in contraction but when the blood outflow velocity is relatively low. Operation of a moving valve in the latter half of systole has been previously described. However, an additional opportunity for moving valve assist during relatively low blood outflow velocity includes a period of time at the very beginning of left ventricle contraction before left ventricle pressure has risen to the level for opening the aortic valve. This time period is referred to as the isovolumic contraction time or phase. The isovolumic contraction phase is illustrated in FIG. 11A, which sets forth the relationship between mechanical activity and electrical activity in the heart. FIG. 11B illustrates a normal EKG with the P wave preceding the start of the QRS complex by approximately 160 milliseconds (ms). To time the beginning of a forward valve movement during the isovolumic contraction phase, the P wave of the electrocardiogram may be used to trigger valve movement. Sensing the P wave of the electrocardiogram provides sufficient anticipation or lead time for starting the motor of a moving valve pump system (for example, motor 120 of pump system 100) and having the moving valve begin its forward stroke at the beginning of the relatively short isovolumic time phase which occurs at the beginning of left ventricle contraction.

The P wave represents the electrical activity of the heart's atria or entrance chambers. As set forth above, P waves typically occur 160 milliseconds before the electrocardiogram's QRS complex, which signals ventricular contraction. P waves can, for example, be sensed by inserting a bipolar sensing lead into right atrium 16 and locating the lead against the atrium's inner wall. There may be time for only one forward stroke during the isovolumic contraction phase. Nonetheless, for moving valve pump systems that must take advantage of periods when left ventricle 14 is in contraction but when the blood outflow velocity is relatively low, operating the moving valve in the isovolumic contraction phase can provide a significant increase in performance. Such a moving valve pump system can, for example, operate the moving valve in the isolvolumic contraction phase and in the latter half of systole. Such pumps can operate the moving valve solely in the isolvolumic contraction phase and in the latter half of systole. FIG. 11C illustrates the effect of moving a moving valve during the isovolumic contraction (one valve stroke) and during the latter half of systole (two valve strokes) upon blood flow.

In the case of a moving valve pump system wherein the drive system of the pump system includes a rotary motor (optionally a speed reducer) and a converter adapted to convert the rotary motion of the rotary motor to the reciprocating motion of the moving valve (for example, pump system 100), the pump system may have sufficient speed/power to pump at any time during a heartbeat, including when blood outflow velocity from the heart is relatively high. However, even in such pump systems, timed operation during periods of relatively low blood outflow from the heart such as the isovolumic period and/or during the latter half of systole can still provide efficiencies and/or other benefits.

Figure 12A:
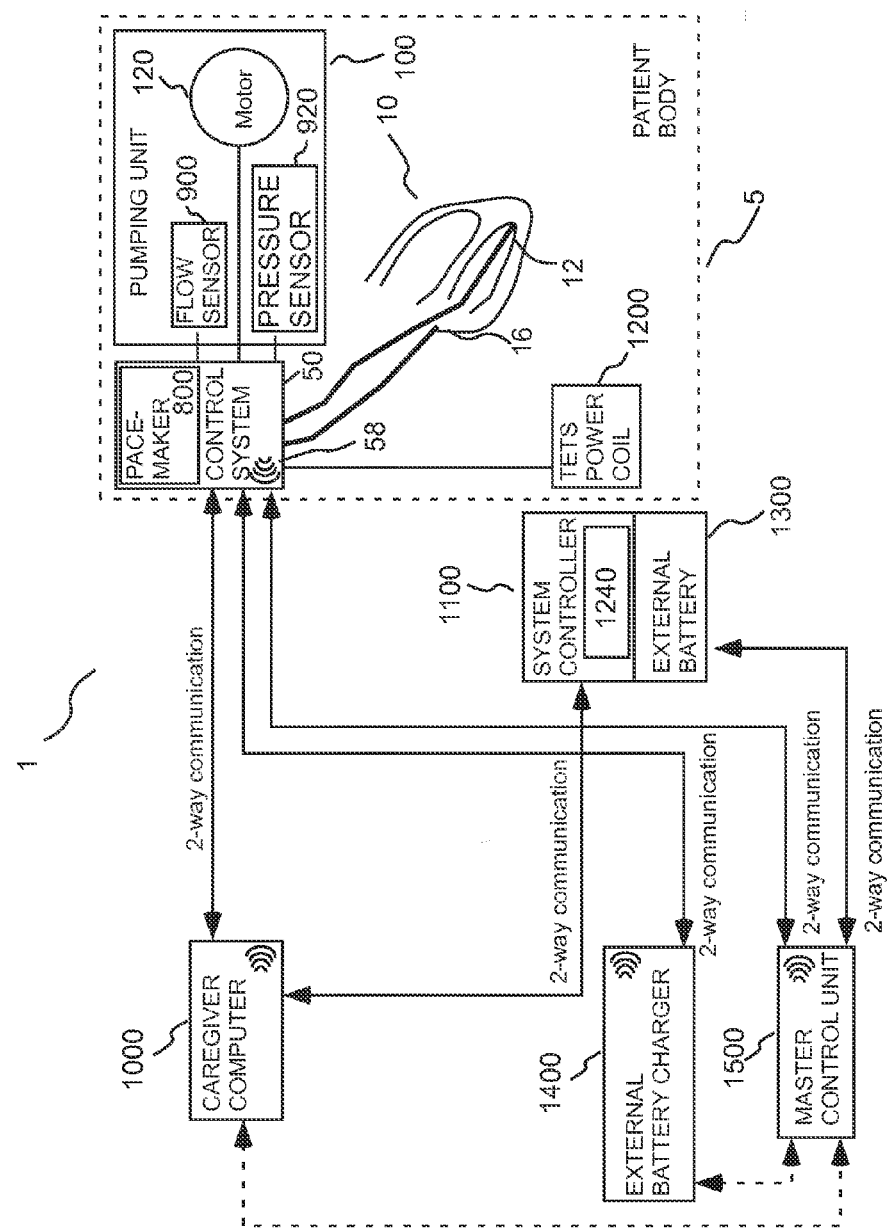
FIG. 12A illustrates an embodiment of a system including a pump system hereof wherein information can be communicated to and from an external system such as a caregivers computer system.
Figure 12B:
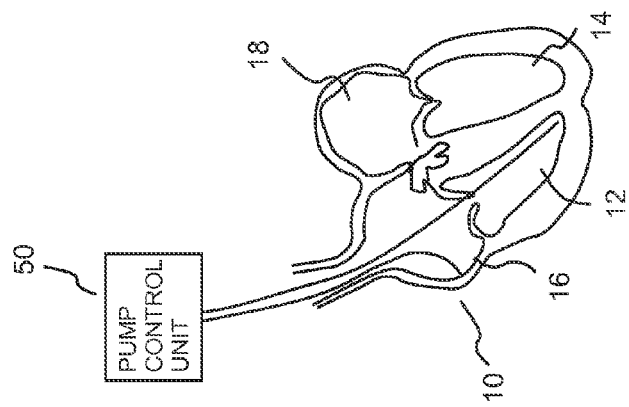
FIG. 12B illustrates an enlarged view of the heart illustrates placement of pacemaker leads from a control system of the system of FIG. 12A.

In the case of both systolic failure and preserved ejection fraction heart failure, a moving valve pump system can be combined with pacemaker circuitry 800 as described above, with at least one pacemaker lead connected with heart 10 (see FIGS. 2, 12A and 12B). In the case of systolic heart failure, the pacemaker lead can sense the P wave to, for example, time valve movement during the isovolumic phase and beyond.

In the case of preserved ejection fraction failure, pacemaker 800 can, for example, be used to increase the heart rate. An increased heart rate (for example, between 90 and 110 beats per minute) combined with moving valve assist to unburden the heart's muscle should increase cardiac output in proportion to the ratio of the paced heart rate to the un-paced heart rate. For example, if the unpaced heart rate is 75 and the paced rate is 105, the expected increase in cardiac output would be 105/75 or 40 percent. The pacing can be either atrial, ventricular or combined atrial ventricular pacing. To do the latter, pacing leads can be placed in contact with both right atrium 16 and right ventricle 12. Atrial ventricular or AV pacing is the most desirable form of pacing because properly timed paced atrial contractions will help provide left ventricle 14 with more blood and more wall stretch than will occur with improperly timed atrial contractions.

Thus, pacemaker 800 can be controlled in combination with or interdependently with pump system 100 or another pump system to achieve a determined or desired level of pump assist/cardiac output. Such control can be effected regardless of the type of heart failure. Moreover, such control can be effected when the pump system is a moving valve pump system or another type of blood flow assist pump system.

Physician and/or other caregiver (sometimes referred to collectively herein as a caregiver) programming capability can, for example, be provided to, for example, adjust parameters to effect proper timing of pump system and/or one or more other parameters of pump system operation to assist the weak heart. Caregiver programming is particularly valuable in embodiments wherein pacing is combined with moving valve assist.

One or more sensors can be placed in operative connection with the blood flowing through the pump system to measure a property of the blood. In a number of embodiments, such a sensor or sensors can measure a property or properties of the blood during assist and absent assist. A blood flow sensor 900 (see, for example, FIG. 4C), integrated into the moving valve pump system, can, for example, be used in determining the instantaneous blood flow going through the pump. Blood flow sensor 900 can, for example, include a thermistor placed within the blood flow (for example, near the center of blood flow). Pump system 100 is used to discuss several embodiments of devices, systems and methods hereof, including sensors to determine blood parameters but one skilled in the art appreciates that such devices, systems and methods are applicable to heart assist pump systems generally. FIGS. 4B, 4C and 21A illustrate flow sensor 900 (for example, a flow velocity sensor) incorporated into pump system 100, which is positioned rearward of the rearwardmost position of valve assembly 300, 300a or 300b. Flow sensor 920 can, for example, alternatively be positioned forward of the forwardmost position of valve assembly 300, 300a or 300b. In the illustrated embodiment, flow sensor 900 extends from curved connective member 205.

The instantaneous flow rate of blood flowing through the moving valve pump, expressed in milliliters per second or liters per minute, can, for example, be determined by electronically processing the resistance related voltage signal coming from the contacts of a thermistor chip placed, for example, in the middle of the cross sectional lumen of the blood flow pathway of a moving valve pump system such as pump system 100. In several embodiments, a square thermistor chip, 70 mils by 70 mils and having a thickness of 11 mils (available, for example, from U.S. Sensor Corp of Orange, Calif.) was used. Such a thermistor experiences a change in its resistance of approximately 4% per degree centigrade temperature change. Each side of the thermistor can, for example, be gold plated. Two gold wires can, for example, be welded to the two opposite sides of the chip. The chip and wire assembly can then be coated with an insulating layer, such as a layer of biocompatible polyurethane. A constant current source providing a low electric current through the gold wires can, for example, be used to slightly heat the thermistor a degree or two above blood temperature. As blood flow passes over and cools the warmed thermistor, the thermistor resistance changes in proportion to the velocity of the blood passing over the thermistor. Because the resistance changes, the voltage required for the constant current changes and that voltage change is indicative of the blood flow rate passing through pump system 100. Such a flow sensing thermistor and associated circuitry may, for example, be calibrated by simultaneously making measurements using, for example, a calibrated ultrasonic flow transducer together with the thermistor sensor and determining the calibration adjustments necessary to make the thermistor signal agree with the calibrated ultrasonic flow transducer.

A pressure sensor 920, can also be incorporated into moving valve pump system 100 or other pump system. As illustrated in FIGS. 4C and 6D, pressure sensor 920 can, for example, be positioned rearward of the rearwardmost position valve assembly 300, 300a or 300b. In several embodiments, pressure sensor 920 was positioned outside of the blood flow within a wall of curved connective portion 205, but was in operative or fluid connection with the blood to experience the pressure thereof via a flexible barrier (comprising, for example, a flexible, biocompatible polymer such as a urethane polymer or polyurethane) between pressure sensor 920 and the blood flow. Like flow sensor 900, pressure sensor 920 can, for example, be useful for control purposes. Output signals from sensors 900 and 920, respectively, representing flow and pressure, when amplified and conditioned by the implanted electronics of control system 50 can, for example, be sent via a high frequency radio signal from the body to, for example, a physician's or other caregiver's computer console 1000. Computer console 1000 can, for example, be a special purpose or a general purpose personal computer. The caregiver can, for example, observe measures of both the flow and pressure (and/or other measure properties of blood or parameters of pump system 100) detected in pump system 100, which can reside in ascending aortic 22 space as described above, either during blood flow assist or absent blood flow assist. With the valve assembly 300, 300*a* or 300*b* of pump system 100 set in the "off" mode, the valve assembly is stationary and in an open state, the caregiver can observe the patient's unassisted blood flow profile and caregiver computer 1000 can, for example, integrate the flow signal to calculate heart stroke volumes as well as cardiac output expressed in liters per minute or LPM terms. The caregiver can then add moving valve assist by activating valve assembly 300, 300*a* or 300*b* using, for example, test modes and timing adjustments to determine which moving valve operating mode is best for patient 5 (for example, to provide a determined or desired assisted cardiac output). Either or both a patient worn system controller 1100 or implanted pump controller 50 can then be programmed for automatic moving valve operation as patient 5 leaves the caregiver's/physician's environment.

Biasing a valve opening to an open position (for example, to a fully open position) as described above in connection with closure members 330, 330*a* and 330*b* can be beneficial, for example, to ensure that blood flow parameters measured in the absence of assist (that is, when the moving valve is stationary) are accurate. In this regard, even partial closure of the moving valve opening can effect measurement of parameters such as flow velocity/rate, pressure etc.

Output from sensors which provide a measurement of one or more parameters of the blood (including, for example, parameters of blood flow) such as sensors 900 and 920 and/or other sensor can be used in setting parameters for pump system 100 as well as for providing closed-loop control of pump system 100. As known in the computer arts, control algorithms, which can include artificial intelligence routines, can be programmed into the processors (for example, microprocessors) of patient worn system controller 1100 and/or implanted pump controller 50, including, for example, if-then statements, as well as other types of automatic logical control. For example, if pressure sensor 920 senses ventricular pressure dropping below 50 mmHg during moving valve assist (that is, during movement or drive of valve assembly 300, 300*a* or 300*b*), this indicates a "pumping the ventricle dry" condition wherein excessive blood is being pumped from left ventricle 14 by pump system 100. Under this condition, the pumping effort can be reduced via adjustment of control of the movement of valve assembly 300, 300*a* or 300*b* (for example, decreasing the number of strokes and/or slowing the stroke speed). During systole, if the ventricular volume drops too low, dangerous arrhythmias or electrical derangements of heart 10 can occur. One or more parameters such as the unassisted flow of blood from the heart, heart rate etc. can, for example, be used to dynamically determine the level of moving valve assist to reach a desired cardiac output for the patient and the timing and/or frequency of the movement of valve assembly 300, 300*a* or 300*b* can be adjusted accordingly. For example, measured outflow of blood from the left ventricle of the heart can be used to time beginning of forward movement of the valve assembly. For example, such outflow increase rapidly early in systole.

In addition to physiologic output signals such as flow and pressure, motor performance parameters or signals can also be sensed and periodically recorded. These signals can, for example, include or be related to motor current, motor commutation, timing events, as well as motor speed and its derivatives of valve speed, valve position and valve acceleration. These signals can, for example, be transmitted to implanted control system 50 via implanted leads connecting control system 50 to pump system 100 (see FIGS. 2 and 12A) and heart 10. Using the known relationship of motor current to motor torque, the system will be capable of determining the force being supplied to the moving valve. By additionally determining/measuring the pressure behind the valve, the system will be capable of, for example, calculating the pressure difference across valve assembly 300, 300*a* or 300*b*. The pressure difference across valve assembly 300, 300*a* or 300*b* can also be measured more directly using an appropriate sensor or sensors. This pressure difference when multiplied by valve assembly velocity and integrated during the forward stroke of valve assembly 300, 300*a* or 300*b* provides valve assembly work and power information. With pump system 100 off, flow and pressure sensing similarly provide unassisted heart work and power performance information. With pump system 100 on, the relative energy contributions of heart 10 and pump system 100 can be calculated and the operating parameters of pump system 100 can be adjusted to provide the best possible outcomes for patient 5 as judged by the caregiver.

In a number of embodiments, the control system is adapted to control movement of the valve on the basis of data regarding position of the valve at a particular time or a derivative thereof (that is, position, velocity, acceleration or a derivative thereof) in combination with data of the measured at least one property of blood from one or more sensors such as a pressure sensor and/or a flow sensor.

An embodiment of a system 1 for use in connection with patient 5 is illustrated in FIGS. 12A and 12B. In this embodiment, implanted pump control unit 50 includes pacing and EKG sensing leads that attach to the right side of heart 10 as describe above. A transcutaneous energy transfer system (TETS) secondary power coil 1200 is implanted and is connected to implanted control system 50 to provide the power to run control system 50 and pump system 100. A system controller 1100 is worn by patient 5 outside of the body and can, for example, include a primary TETS coil 1240. Transcutaneous Energy Transfer or TET is a system including two coils (internal coil 1200 and external 1240) that transmit power via magnetic force/induction from a patient-worn, external battery 1300 across the skin of patient 5 without requiring piercing of the skin. External battery 1300 can, for example, be removable and rechargeable. Internal TETS coil 1200 receives the power and transmits it to control system 50 for control and pump system operation. An external battery pack charging unit 1400 can, for example, be used by patient 5 to maintain charge of multiple external batteries 1300 required to power the system in continuous use.

Two-way communications between implanted control system 50 and other internal and/or external components can, for example, be effected wirelessly via radio waves and/or other energy by an implanted communication system 58 which is in communicative connection with control system 50. A master control unit 1500 can, for example, reside at the manufacturer and can be used to program and evaluate system components. Master control unit 1500 can, for example, communicate with caregiver computer 1000, battery charger 1400 and/or other components via, for example, a local area network (LAN), a wide area network (WAN) or the internet.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A system for assisting blood flow in a patient, comprising:
   an implantable pump system for assisting in blood flow from the heart:
   an implantable control system for communicative connection with the implantable pump system comprising a pacemaker system that is operative to control heart rate and the pump system interdependently to achieve a determined level of blood flow assist, the control system being adapted to increase the heart rate of the patient to above a normal heart rate for the patient under the present conditions of the patient via the pacemaker while controlling the pump system to achieve the determined level of blood flow assist based upon the increased heart rate and a level of assist provided by the pump system, wherein the pacemaker is adapted to increase the heart rate to a rate at least 20 percent higher than the normal heart rate for the patient under the present conditions of the patient.

2. The system of claim 1 wherein the pacemaker is adapted to increase heart rate 20 to 50% above the normal heart rate of the patient under the conditions of the patient to achieve a determined level of blood flow assist.

3. The system of claim 1 wherein the pump system is a moving valve pump system comprising a valve assembly which is movable within the blood flow path of the pump system.

4. A method for assisting blood flow in a patient, comprising:
   providing an implantable pump system for assisting in blood flow from the heart:
   providing an implantable control system for communicative connection with the implantable pump system comprising a pacemaker system that is operative to control heart rate and the pump system interdependently to achieve a determined level of blood flow assist, and
   increasing the heart rate of the patient to above a normal heart rate for the patient under the present conditions of the patient via the pacemaker while controlling the pump system to achieve the determined level of blood flow assist based upon the increased heart rate and a level of assist provided by the pump system, wherein heart rate is increase to a rate at least 20 percent higher than the normal heart rate for the patient under the present conditions of the patient.

5. The method of claim 4 wherein the heart rate is increased 20 to 50% above the normal heart rate of the patient under the present conditions of the patient to achieve a determined level of blood flow assist.

6. The method of claim 4 wherein the implantable pump system is a moving valve pump system comprising a valve assembly which is movable within the blood flow path of the pump system.

* * * * *